United States Patent [19]

Minchey et al.

[11] Patent Number: 5,415,867
[45] Date of Patent: May 16, 1995

[54] HIGH RATIO ACTIVE AGENT: LIPID COMPLEX

[75] Inventors: Sharma R. Minchey, Monmouth Junction; Christine E. Swenson, Princeton Junction, both of N.J.; Andrew S. Janoff, Yardley, Pa.; Lawrence Boni, Monmouth Junction, N.J.; Kathy A. Stewart, Morrison, Ill.; Walter Perkins, Plainsboro, N.J.

[73] Assignee: The Liposome Company, Inc., Princeton, N.J.

[21] Appl. No.: 105,764

[22] Filed: Aug. 11, 1993

Related U.S. Application Data

[63] Continuation of Ser. No. 355,028, May 22, 1989, abandoned, which is a continuation-in-part of Ser. No. 183,793, Apr. 20, 1988, abandoned, and Ser. No. 196,913, May 20, 1988, abandoned.

[51] Int. Cl.$^6$ .............................. A61K 9/127
[52] U.S. Cl. ...................... 424/450; 264/46
[58] Field of Search ............ 424/4.5, 450; 264/4.1, 264/4.3, 4.6; 514/963

[56] References Cited

U.S. PATENT DOCUMENTS

| | | | |
|---|---|---|---|
| 4,137,317 | 1/1979 | Paris et al. | 514/86 X |
| 4,192,859 | 3/1980 | Mackaness et al. | 424/5 |
| 4,235,871 | 11/1980 | Papahadjopoulos et al. | 424/450 |
| 4,438,052 | 3/1984 | Weder et al. | 264/4.6 |
| 4,522,803 | 6/1985 | Lenk et al. | |
| 4,544,545 | 10/1985 | Ryan et al. | 424/9 X |
| 4,567,034 | 1/1986 | Charles et al. | 424/5 |
| 4,588,578 | 5/1986 | Fountain et al. | 428/402.2 X |
| 4,673,567 | 6/1987 | Jizomoto | 264/4.3 X |
| 4,708,861 | 11/1987 | Popescu et al. | 428/402.2 X |
| 4,731,210 | 3/1988 | Weder et al. | 264/4.3 |
| 4,735,795 | 4/1988 | Robinson et al. | 424/5 |
| 4,753,788 | 6/1988 | Gamble | 424/450 X |
| 4,830,858 | 5/1989 | Payne et al. | |
| 5,312,615 | 5/1994 | Schneider et al. | 424/5 |

FOREIGN PATENT DOCUMENTS

| | | |
|---|---|---|
| 158441 | 10/1985 | European Pat. Off. |
| 0158441 | 10/1985 | European Pat. Off. ........ A61K 9/50 |
| 0314764 | 9/1992 | European Pat. Off. ........ A61K 9/50 |
| 85/000515 | 2/1985 | WIPO ................. 424/450 |
| 8500515 | 2/1985 | WIPO ................. 424/450 |

OTHER PUBLICATIONS

Yasuhara et al., Chem. Pharm. Bull., vol. 25, No. 4, pp. 675–679 (1977).
Desiderio et al., "Liposome-encapsulated cephalothin in the treatment of experimental murine Salmonellosis", RES: Journal of the Reticuloendothelial Society, vol. 34, pp. 279–287 (1983).
Chem. Abs., vol. 87, No. 11, Yasuhara et al., Abs. #78182(b) 1977.
Chem. Abs., vol. 99, No. 24, Desiderio et al., Abs. No. 200449j, 1983.
Chem. Abs., vol. 102, No. 24, Pourkavoos et al., Abs. No. 209213r, 1984.
Desiderio, et al., "Intraphagocytic Killing of fSalmonella typhimurium by Liposome-Encapsulated Cephalothin", J. Infec. Dis., 148(3), 1983, 563–570.

Primary Examiner—Richard D. Lovering
Assistant Examiner—John M. Covert
Attorney, Agent, or Firm—Joanne Longo Feeney

[57] ABSTRACT

High ratio active agent:lipid complexes, their preparation and use are disclosed. Particular reference is made to cephalosporin:lipid complex and iodinated contrast agent:lipid complex. Use of high ratio cephalosporin:lipid complex in bacterial prophylaxis, and particularly bacteremia prophylaxis, including a method of preventing bacterial infection in an animal over an extended period comprising the step of administering to said animal a high ratio cephalosporin:lipid complex is further disclosed as is the use of high ratio iodinated contrast agent:lipid complex in X-ray applications.

49 Claims, 12 Drawing Sheets

• EPC
○ CHS
■ α-THS

■ Intravenous EPC Complex
□ Intravenous Free Drug
● Subcutaneous CHS-tris complex
○ Subcutaneous Free Drug ○ Cefazolin in Conventional Aqueous solution
□ Cefazolin in DPPC complex

HIGH RATIO ACTIVE AGENT: LIPID COMPLEX

This application is a continuation of application Ser. No. 07/355,028 filed on May 22, 1989, now abandoned, which application is a continuation-in-part of U.S. Patent Application Ser. No. 183,793 filed Apr. 20, 1988, now abandoned, and U.S. Patent Application Ser. No. 196,913 filed May 20, 1988, now abandoned.

FIELD OF THE INVENTION

This invention is concerned with high ratio active agent:lipid complexes, their preparation and use. Particular reference is made to cephalosporin:lipid complex and iodinated contrast agent:lipid complex. More particularly disclosed is a high ratio cephalosporin:lipid complex comprising a rigid lipid and a cephalosporin. A method of preparation of high active agent:lipid complexes is also disclosed. Use of cephalosporin:lipid complex in bacterial prophylaxis, and particularly bacteremia prophylaxis, including a method of preventing bacterial infection in an animal over an extended period comprising the step of administering to said animal a high ratio cephalosporin:lipid complex is further disclosed. In one embodiment this invention includes such prophylaxis by maintaining over an extended period an available drug level of at least about a minimum inhibitory concentration. Another embodiment is the use of high ratio iodinated contrast agent:lipid complex in X-ray applications.

BACKGROUND OF THE INVENTION

A basic element of the practice of therapeutics is the administration of active agents to subjects of treatment. In many situations the problem of administration is one of delivering enough of an active agent in an efficient manner to the sight of action. Liposome encapsulation has, in some instances, offered effective delivery of active agents. However particular active agents have not been efficiently delivered or not delivered in high enough concentrations or in concentrations relative to accompanying lipid that entailed excessive lipid administration. Thus a method of forming a high ratio active agent:lipid complex is of great interest. Active agents (also termed bioactive agents) are for example, drugs hormones, proteins, dyes, vitamins, or imaging agents. As used in the present invention, the term active agent is understood to include any compound having biological activity, e.g., drugs and other therapeutic agents such as peptides, hormones, toxins, enzymes, neurotransmitters, lipoproteins, glycoproteins, immunomodulators, immunoglobulins, polysaccharides, cell receptor binding molecules, nucleic acids, polynucleotides, and the like, as well as including biological tracer substances such as dyes, radio-opaque or radio-contrast agents for X-ray imaging (collectively "contrast agents"), and fluorescent agents.

Prophylactic use of antimicrobial agents is a widely discussed course of pharmaceutical treatment, e.g., "Prophylactic Use of Antimicrobial Agents in Adult Patients", *Mayo Clin Proc,* 62:1137–1141 (1987). In appropriate cases, rheumatic fever, bubonic plague, malaria and other diseases are treated prophylactically. A particularly well recognized area of antimicrobial, and especially antibacterial, prophylaxis is the preoperative use of antimicrobial agents. Generally, it has been a concomitant of surgical prophylaxis that the antimicrobial agent be given only during or at most no more than about three hours before surgery.

A central consideration in the administration of prophylactic drug therapy is the ability and ease with which a "minimum inhibitory concentration" ("MIC") of a particular antimicrobial agent may be established and the interval over which such level may be maintained in a subject animal. An MIC is defined as the lowest level of a particular antimicrobial agent (whether antibacterial, anti-infective or other) that will prevent proliferation of the pathogenic organism being treated. An MIC may be established in a physiological fluid such as cerebro-spinal fluid, serum or plasma or in tissue, and particularly tissue at the site of infection (such as the reticulo-endothelial system in disseminated infections).

Conventionally, the MIC for a particular organism is measured in an in vitro system, and is expressed in terms of the amount of drug (by weight) per amount (usually volume) of material in which the drug is dispersed. For a drug to exert a therapeutic or prophylactic effect in vivo the concentration of such drug in vivo will usually be required to be about equal to or greater than the MIC as measured in vitro. Furthermore, the greater the concentration of drug above the MIC and the greater the period of time the in vivo drug level exceeds the MIC, the greater the therapeutic response.

To express the parameter of time over which an in vivo plasma concentration of antibiotic equals or exceeds the MIC of a challenging pathogen the term T greater than $MIC_p$ will be used and written as $T_p$.

To express the parameter of time over which an in vivo tissue concentration of antibiotic equals or exceeds the MIC of a challenging pathogen the term T greater than $MIC_t$ will be used and written as $T_t$.

Liposomes are completely closed lipid bilayer membranes containing an entrapped aqueous volume. Liposomes may be unilamellar vesicles (possessing a single bilayer membrane) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient toward the aqueous phase.

The original liposome preparation of Bangham, et al. (*J. Mol. Biol.,* 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.,* 1968, 135:624–638), and large unilamellar vesicles.

Unilamellar vesicles may be produced using an extrusion apparatus by a method described in Cullis et al., PCT Application No. WO 86/00238, published Jan. 16, 1986, entitled "Extrusion Technique for Producing Unilamellar Vesicles" incorporated herein by reference. Vesicles made by this technique, called LUVETS, are extruded under pressure through a membrane filter. LUVETs, being usually of about 500 nm diameter or less, and frequently about 100 nm, are preferred liposomes of the instant invention. LUVETs will be understood to be included in the term "unilamellar vesicle".

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,588,578 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies". The teachings of these references as to preparation and use of liposomes are incorporated herein by reference.

Liposomes with a diameter of about 500 nm or less are termed "small liposomes". Similarly, the cephalosporin:lipid complexes of this invention will be termed "small" at a diameter of about 500 nm or less. Diameter in describing a population of liposomes or vesicles will be understood to reflect a range of diameters.

The cephalosporin:lipid complexes of this invention are in the form of liposomes at lower drug to lipid ratios. At higher drug to lipid ratios the complexes appear to retain the bilayer organization of liposomes but, in electronmicrograph, may be other than completely closed. The term "complex" is to be understood to encompass both liposomes as well as the higher ratio cephalosporin:lipid entities even if such entities differ from liposomes in having incompletely closed bilayers or other anomalies.

Iodinated contrast agents also form complexes with lipids as an aspect of this invention and exhibit high capture volumes of up to about 20 ul/umole lipid. These appear to be in the form of liposomes and are predominately unilamellar and uniform in size at about 0.5 microns. Prior to this invention, contrast agent:lipid ratios of about 2.7:1 were reported as to non-ionic iodinated contrast agents and 1:1 as to negatively charged iodinated contrast agents (e.g., diatrizoate).

Over the past ten years, there have been several groups attempting to develop particulate contrast agents which would specifically opacify organs of the RE system, Seltzer, S. E., Liposomes as Drug Carriers, Gregoriadis, G., ed., pp 509–525 (John Wiley and Sons, Ltd. New York 1988). One such application involves the detection of metastatic lesions in the liver by x-ray computed tomography (CT). Conventionally a patient is dosed with a water soluble contrast agent before CT scanning, but because the agent has essentially equal access to both normal and tumor tissue, there is minimal if any contrast between the two tissues. However, if a patient were dosed with particulate contrast agent, the Kupffer cells of the liver would phagocytose the agent causing the cells to become opaque leaving the tumor cells dark. Several particulate agents have been developed and used in humans but these agents have some associated toxicities presumably due to their extended tissue residence time. Particulate contrast agents are reported in Cohen, Z., et al J. Comput. Assist. Tomogr., 5:843–7 (1981); Miller, D. L., et al., AJR, 143:235–243 (1984); Longino, M. A., et al., J. Comput. Assist. Tomogr., 7:775–9 (1983); Mattrey, R. F., et al., Radiology, 145:755–8, (1983); Violante, M. R., et al., Invest. Radiol., 16:40–5 (1981). Another means of achieving a particulate contrast agent is entrapment of the agent in liposomes, Havron, H. A., et al., Radiology, 140:507–11 (1981). The lipid dose required by these preparations is too high for application to humans. The highest reported iodine:lipid ratio in the literature for diatrizoate, the most commonly used contrast agent, is about 1:1 (wt/wt).

In some applications admixing a lipid with cholesterol will reduce the entrapment of cephalosporin. This is potentially the result of cholesterol dispersing in the lipid bilayer and decreasing bilayer rigidity. Lipids are characterized in having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient toward the aqueous phase. The tail region may be comprised of fatty acyl chains (also denoted as carbon chains), or a single such chain as in the case of alpha-tocopherol hemi-succinate. Examples of lipids are the phospholipids such as phosphatidylcholine (PG) (egg phosphatidylcholine is denoted EPG), phosphatidylethanolamine (PE), phosphatidylserine (PS), phosphatidylglycerol (PG), phosphatidic acid (PA), phosphatidylinositol (PI), sphingomyelin (SPM), and the like, alone or in combination and particularly in hydrogenated or saturated form of the carbon chain. The phospholipids can be synthetic or derived from natural sources such as egg or soy. Synthetic phospholipids include dymyristoylphosphatidylcholine (DMPC) and dimyristoylphosphatidylglycerol (DMPG). The preferred lipids of this invention are those with saturated carbon chains of at least about 16 carbon units as well as nonphospholipids such as digalactosyldiglyceride. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method Blown in the art for preparing liposomes containing these sterols. In particular, see the procedures of Janoff et al., U.S. Pat. No. 4,721,612 issued Jan. 26, 1988, entitled "Steroidal Liposomes," and Janoff et al., PCT Publication No. WO87/02219, published Apr. 23, 1987, entitled "Alpha-Tocopherol Based Vesicles," filed Sep. 24, 1986, respectively, corresponding to U.S. Pat. No. 4,861,580, issued Aug. 29, 1989. Additional known lipids are glycolipids.

SUMMARY OF THE INVENTION

In a broad aspect this invention presents a method of preparing high ratio active agent:lipid complex comprising a lipid and an active agent comprising the step of evaporating to monophase but not to substantial dryness a mixture of lipid and active agent in a monophasic solvent system comprising aqueous phase, aqueous miscible organic solvent and lipid.

This invention includes a high ratio cephalosporin:lipid complex comprising a lipid and a cephalosporin, and in one embodiment the lipid is a rigid lipid such as wherein the lipid consists of a head group and two carbon chains said chains are saturated and of a length of at least about 16 carbon units. One rigid lipid is dipalmitoylphosphatidylcholine.

In a particular embodiments of the high ratio cephalosporin:lipid complex the cephalosporin comprises at least 20%, 30%, 40% or 50% of the complex (w/w—designating the weight of a component as to the total weight). In one embodiment the lipid is dipalmitoylphosphatidylcholine, and potentially up to about 80% (w/w) of the complex. In yet another embodiment of the cephalosporin:lipid complex the lipid comprises of a head group and two carbon chains said chains are saturated and of a length of at least about 16 carbon units.

In particular embodiments the cephalosporin of the high ratio cephalosporin:lipid complex is cefazolin, cephapirin, cephalothin, cefaclor, cephaloridine, cephoxazole, cefoxitin, cephradine, cephalexin, cephaloglycine, cefuroxime, cefmenoxime, or cephalonium, particularly cefazolin.

The invention also includes a method of preparing high ratio cephalosporin:lipid complex comprising a rigid lipid and a cephalosporin comprising the step of evaporating to monophase but not to substantial dryness a mixture of rigid lipid and cephalosporin in a monophasic solvent system comprising aqueous phase, aqueous miscible organic solvent and lipid. In one embodiment to the method the monophasic solvent system is about equal amounts (v/v) of (a) aqueous phase of drug, (b) ethanol and (c) chloroform and said lipid.

In a particular embodiment the method comprises the step of evaporating to monophase but not to substantial dryness a mixture of said lipid and cephalosporin in a solvent system comprising about equal amounts (v/v) aqueous phase (drug-and-lipid):ethanol:chloroform, including evaporating solvent by positive pressure at about 30 to about 37° C. In the practice of one embodiment of this invention the method comprises about two administrations each day or less. In further embodiments the method comprises maintaining over an extended period an available cephalosporin level of at least a minimum inhibitory concentration ("MIC") of the cephalosporin in an animal, and specifically wherein the the cephalosporin level is at least about 4 times the MIC. In some embodiments the MIC is measured as a blood plasma or serum level or tissue level. In some embodiments administration is intramuscularly, intraperitoneally, intravenously or subcutaneously. In the practice of this method the cephalosporin may comprise any or all of cefazolin, cephapirin, cephalothin, cefaclor, cephaloridine, cephoxazole, cefoxitin, cephradine, cephalexin, cephaloglycine, cefuroxime, cefmenoxime or cephalonium. In certain embodiments of the method wherein the cephalosporin comprises cefazolin the method further comprises administering said cefazolin at a dosage of about 20–150 mg base weight per kilogram animal body weight per day or the maintained available cephalosporin level of cefazolin is at least about 0.5, 5, or 50 ug (base weight)/ml plasma or at least about 0.5 ug (base weight)/mg tissue (RES tissue such as liver or spleen).

In particular embodiments of the method the resulting cephalosporin:lipid complex is at least about 30%, 40%, or 50% (w/w) cephalosporin. In some embodiments of the method wherein the lipid is comprised of a head group and two carbon chains said chains being saturated and of a length of at least about 16 carbon units or the lipid is dipalmitoylphosphatidylcholine, such as up to about 80% (w/w) of the complex. In the practice of the method the cephalosporin is in particular embodiments cefazolin, cephapirin, cephalothin, cefaclor, cephaloridine, cephoxazole, cefoxitin, cephradine, cephalexin, cephaloglycine, cefuroxime, cefmenoxime or cephalonium and particularly cefazolin.

The method of this invention yet further includes a method of bacterial infection prophylaxis in an animal, including a human, comprising the step of administering to said animal a bacterial infection prophylaxis effective amount of cephalosporin:lipid complex, and in one embodiment wherein the complex is a high ratio cephalosporin:lipid complex, the lipid is a rigid lipid.

A particular embodiment of the prophylaxis method of this invention is to bacteremia. In the practice of one embodiment of this invention the method comprises about two administrations each day or less. In further embodiments the method comprises maintaining over an extended period an available cephalosporin level of at least a minimum inhibitory concentration ("MIC") of the cephalosporin in an animal, and specifically wherein the the cephalosporin level is at least about 4 times the MIC. In some embodiments the MIC is measured as a blood plasma or serum level or tissue level. In some embodiments administration is intramuscularly, intraperitoneally, intravenously or subcutaneously. In the practice of this method the cephalosporin may comprise any or all of cefazolin, cephapirin, cephalothin, cefaclor, cephaloridine, cephoxazole, cefoxitin, cephradine, cephalexin, cephaloglycine, cefuroxime, cefmenoxime or cephalonium. In certain embodiments of the method wherein the cephalosporin comprises cefazolin the method further comprises administering said cefazolin at a dosage of about 20–150 mg base weight per kilogram animal body weight per day or the maintained available cephalosporin level of cefazolin is at least about 0.5, 5, or 50 ug (base weight)/ml plasma or at least about 0.5 ug (base weight)/mg tissue (RES tissue such as liver or spleen).

In particular embodiments of the method the resulting cephalosporin:lipid complex is at least about 30%, 40%, or 50% (w/w) cephalosporin. In some embodiments of the method wherein the lipid is comprised of a head group and two carbon chains said chains being saturated and of a length of at least about 16 carbon units or the lipid is dipalmitoylphosphatidylcholine, such as up to about 80% (w/w) of the complex. In the practice of the method the cephalosporin is in particular embodiments cefazolin, cephapirin, cephalothin, cefaclor, cephaloridine, cephoxazole, cefoxitin, cephradine, cephalexin, cephaloglycine, cefuroxime cephmenoxime or cephalonium and particularly cefazolin.

A particular embodiment of the prophylaxis method of this invention is to disseminated bacterial infections involving the reticulo-endothelial system. In the practice of one embodiment of this invention the method comprises about two administrations each day or less. In further embodiments the method comprises maintaining over an extended period an available cephalosporin level of at least a minimum inhibitory concentration ("MIC") of the cephalosporin in an animal, and specifically wherein the the cephalosporin level is at least about 4 times the MIC. In some embodiments the MIC is measured as a blood plasma or serum level or tissue level (such as RES tissue, e.g., liver or spleen). In some embodiments administration is intramuscularly, intraperitoneally, intravenously or subcutaneously. In the practice of this method the cephalosporin may comprise any or all of cefazolin, cephapirin, cephalothin, cefaclor, cephaloridine, cephoxazole, cefoxitin, cephradine, cephalexin, cephaloglycine, cefuroxime, cefmenoxime or cephalonium. In certain embodiments of the method wherein the cephalosporin comprises cefazolin the method further comprises administering said cefazolin at a dosage of about 20-150 mg base weight per kilogram animal body weight per day or the maintained available cephalosporin level of cefazolin is at least about 0.5, 5, or 50 ug (base weight)/ml plasma or at least about 0.5 ug (base weight)/mg tissue (RES tissue such as liver or spleen).

In particular embodiments of the method the resulting cephalosporin:lipid complex is at least about 30%, 40%, or 50% (w/w) cephalosporin. In some embodiments of the method wherein the lipid is comprised of a head group and two carbon chains said chains being saturated and of a length of at least about 16 carbon units or the lipid is dipalmitoylphosphatidylcholine, such as up to about 80% (w/w) of the complex. In the practice of the method the cephalosporin is in particular embodiments cefazolin, cephapirin, cephalothin, cefaclor, cephaloridine, cephoxazole, cefoxitin, cephradine, cephalexin, cephaloglycine, cefuroxime, cefmenoxime or cephalonium and particularly cefazolin. A particular embodiment comprises prophylaxis for the bacteria *Mycobacterium sp.* or *Salmonella sp.* A further embodiment of this invention is prophylaxis directed to bacterial osteomyelitis.

An important aspect of this invention is a high ratio iodinated contrast agent:lipid complex comprising a lipid and an iodinated contrast agent, particularly wherein the lipid is a rigid lipid but also with unsaturated lipid such as phosphatidylcholine. In some embodiments the contrast agent is at least about 2:1 (Iodine w/w), or at least about 4:1 (Iodine w/w) or at least about 8:1 (Iodine w/w). In some instances the lipid comprises a head group and two carbon chains said chains are saturated and of a length of at least about 16 carbon units such as dipalmitoylphosphatidylcholine which comprises as little as about 20 to about 7% (w/w) of the complex. Useful contrast agents are without limitation diatrizoate, iocetamic acid, iodamide, iodoximate, iohexol, iopamide, iopamidol, iopanoic acid, iophendylate, iothalamate, iothalamic acid, ipodate, metrizamide or tyropanate and salts thereof.

This invention also includes a method of preparing high ratio active agent:lipid complex wherein the active agent is an iodinated contrast agent comprising the step of evaporating to monophase but not to substantial dryness a mixture of lipid and contrast agent, in a monophasic solvent system comprising aqueous phase, aqueous miscible organic solvent and lipid. In one embodiment of this method wherein the monophasic solvent system is about equal amounts (v/v) of (a) aqueous phase of contrast agent (b) ethanol and (c) chloroform and said lipid. Also, optionally, further comprises evaporating solvent by positive pressure at about 30° to about 75° C. By this method the contrast agent of the resulting contrast agent:lipid complex is at least about 2:1 (Iodine w/w) or at least about 4:1(Iodine w/w) or at least about 8:1 (Iodine w/w/). Rigid lipids are used in this method such as wherein the lipid comprises of a head group and two carbon chains said chains being saturated and of a length of at least about 16 carbon units, particularly wherein said dipalmitoylphosphatidylcholine comprises as little as about 20% to about 7% (w/w) of the complex. Also useful in the method is wherein the lipid comprises phosphatidylcholine such as egg or soy phosphatidylcholine. Particular contrast agents of the method are diatrizoate, iocetamic acid, iodamide, iodoximate, iopamide, iopamidol, iopanoic acid, iophendylate, iothalamate, iothalamic acid, ipodate calcium, ipodate sodium, metrizamide or tyropanate and salts thereof.

An additional aspect of the invention is a method of increasing X-ray density in an animal, including a human, comprising the step of administering to said animal an X-ray density increasing effective amount of iodinated contrast agent:lipid complex such as wherein the lipid is a rigid lipid as well as wherein the contrast agent is diatrizoate, iocetamic acid, iodamide, iodoximate, iopamide, iopamidol, iopanoic acid, iophendylate, iothalamate, iothalamic acid, ipodate calcium, ipodate sodium, metrizamide or tyropanate and salts thereof. In some applications the contrast agent comprises diatrizoate further comprising administering said diatrizoate at a dosage of about 500 mg or about 1 gm iodine per kilogram animal body weight per day. One embodiment is wherein the increase in X-ray density is to the liver.

DETAILED DESCRIPTION OF THE INVENTION

Experiments in animals have shown that cephalosporin associated with lipid, such as in a liposome or in a cephalosporin:lipid complex, can dramatically alter the distribution of cephalosporin in the body and their rate of clearance. These pharmacokinetic differences, as well as other, less well understood effects, can result in prolonged prophylactic levels of cephalosporin, reduced toxicity and/or enhanced efficacy of the cephalosporin associated with a lipid.

Figure 1:
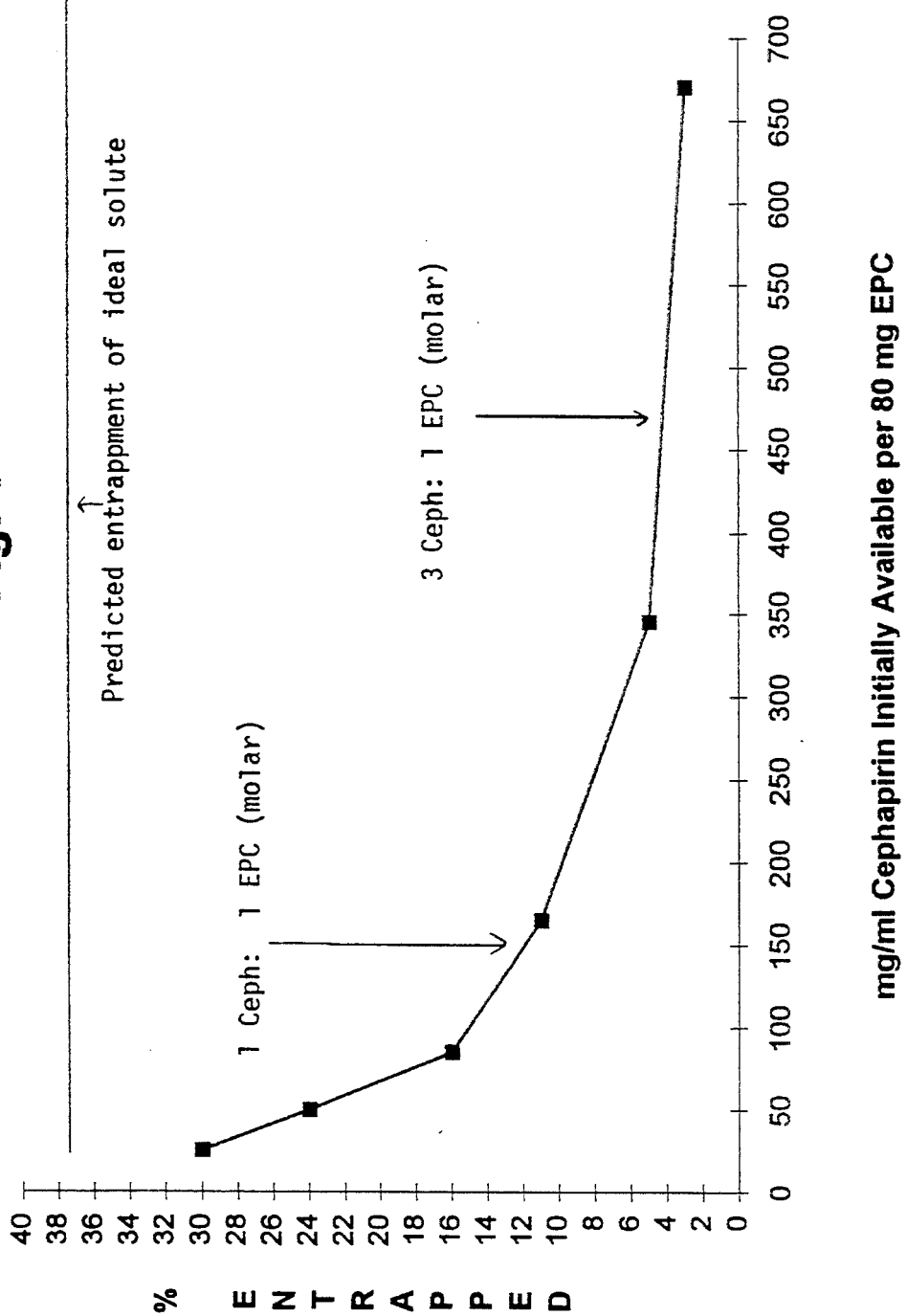
FIG. 1 shows the declining entrapment of cephapirin sodium in egg phosphatidylcholine MPVs vs. drug concentration.
Figure 2:
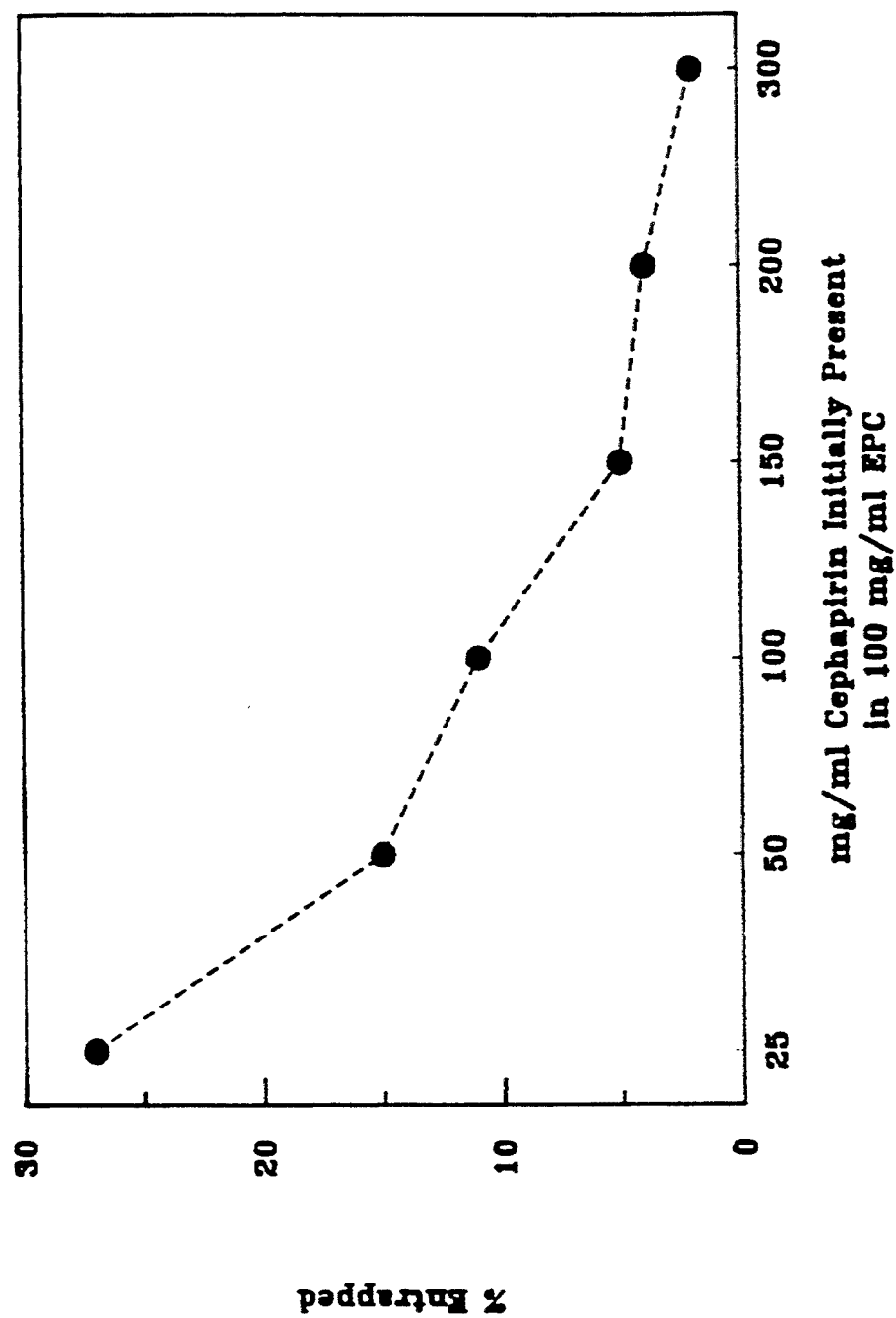
FIG. 2 shows the entrapment of cephapirin sodium in egg phosphatidylcholine FATMLVs vs. drug concentration.

However, the entrapment of cephalosporins into liposomes (or complexes) is typically a low percentage of available drug. As shown in FIG. 1 the entrapment of the cephalosporin cephapirin in the lipid egg phosphatidylcholine decreases with increasing amounts of cephalosporin. The decreasing entrapment indicates a deleterious effect on entrapment by high concentrations of cephalosporin.

"High ratio cephalosporin:lipid complex" is at least about 20% cephalosporin as compared to lipid (w/w). In some embodiments with cephalosporin these are of at least about 30%, and up to about 50% or more of cephalosporin (w/w). High ratio cephalosporin:lipid is particularly useful in cephalosporin therapy for several reasons. First with conventional ratio cephalosporin:lipid the physical mass of the unit lipid dosage is inconvenient for administration if not prohibitive of administration. A typical cephalosporin dose is 4 g/day. For an adult at previously reported ratios of 0.14 g (cephalosporin):1 g (lipid) the unit dosage would be about 32 g of drug and lipid. The usual mode of administration would require admixture with a pharmaceutically acceptable carrier resulting in a unit dosage that was at best unwieldly. Reducing this bolus by a substantial amount of up to about 75% or more is a particular advantage of this invention. Second, toxicity may be associated with administration of large amounts of lipid which is reduced by reducing the amount of lipid administered. Third, the cost of a concentrated dose is substantially lessened by reducing the required amount of lipid. An additional benefit of the instant invention is the high percentage of drug available in a drug:lipid complex preparatory mixture is entrapped in the final complex, which further reduces the cost of the final cephalosporin:lipid preparation.

High ratio contrast agent:lipid complex will be in excess of about 2.7:1 (Iodine w/w) for nonionic contrast agents and in excess of about 1:1 (Iodine:lipid wt/wt) for ionic contrast agents (negatively charged).

Figure 3:
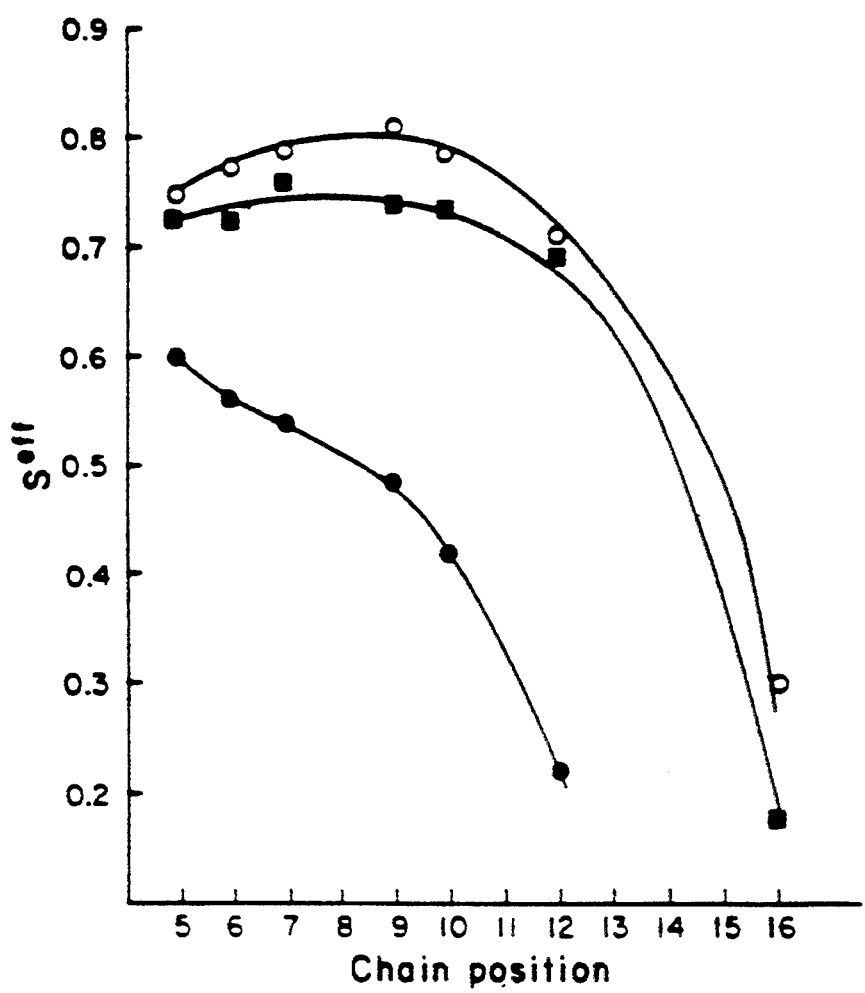
FIG. 3 shows flexibility profiles of multilayered vesicles of EPC, CHS and alpha-THS in defining rigid lipids. The order parameters were obtained by spin labeling the vesicles with a series of doxylstearic acids where the doxyl reporter group was present at different positions along the fatty acid chain. Spectra obtained showed no evidence of unincorporated label.
Figure 4:
FIG. 4 shows high ratio 1:2 (w/w) cefazolin:dipalmitoylphosphatidylcholine complex in electronmicrograph.

In the present invention, the term rigid lipid as used herein shall mean lipids of a flexibility about equal to or less than that of egg phosphatidylcholine. Rigidity is easily determined by methods well known in the art. For example, FIG. 3 expresses rigidity in the spin labeling of lipids in complexes via a doxyl reporter group. As represented in FIG. 3 rigid lipids are those with an order parameter about equal to that of EPC or greater therefore closer to an order parameter of 1 (above of EPC in FIG. 3).

Particularly included as rigid lipids are those with a head group and two carbon chains said chains being of a length of at least about 16 carbon units where the chains are saturated. Such lipids as dipalmitoylphosphatidylcholine (DPPC) and distearoylphosphatidylcholine are in this group. Also, cholesterol hemisuccinate tris(hydroxymethyl)aminomethane ($CHS_{tris}$) and the like are rigid lipids.

The preparation of high ratio active agent:lipid complex, such as with either a cephalosporin or a contrast agent may be accomplished by a modification of the method described in U.S. Pat. No. 4,588,578 entitled "Lipid Vesicles Prepared in a Monophase" the teachings of which are incorporated herein by reference. The vesicles prepared in a monophase are referred to as monophasic vesicles or "MPVs". Monophasic vesicles arise from a novel preparatory process using a monophasic solvent system. The monophasic solvent system is comprised of three components—(1) lipid, (2) aqueous miscible organic solvent and (3) aqueous component. To produce the novel monophasic vesicle these components are mixed to form a monophase prior to removal of the organic solvent. After removal of the organic solvent a drug-lipid film is formed which upon hydration forms monophasic vesicles.

The modified MPV process entails practicing the MPV process at a relatively high initial aqueous volume generally from about 8:1 to about 1:1 (v/v) of aqueous active agent (e.g., cephalosporin) to organic solvent. In the practice of the method of forming high ratio active agent:lipid complex the initial mixture of the monophasic solvent system must pass through a monophase stage whether or not the solvent system begins as a monophase. The term "monophase" shall mean a combination of 2 or more solvents which upon mixing result in a clear solution of constant composition. In practice 2 immiscible solvents which upon mixing form a biphasic system are converted into monophase by the addition of a third solvent that is miscible in both of the original solvents. For example chloroform and water form a biphasic system upon mixing, but form a monophase upon addition of sufficient ethanol.

The central modification of the MPV process is the step of maintaining the active agent (such as cephalosporin or contrast agent) and lipid as hydrated at all times. This hydrated material is the complex of the invention which is usefully diluted into concentrations more convenient for pharmaceutical unit dosage form. The modification of maintaining the material as hydrated then avoids the usual end point of removing all of the aqueous component and forming an active agent:lipid film. That the monophase is hydrated is easily determined simply by observing the material during the evaporative step. The presence of a gel like material indicates that water is still present, whereas if all water is removed a lipid-active agent film will be formed on the vessel containing the material. The foregoing procedure markedly increased the percentage of active agent entrapped relative to active agent available. This procedure also resulted in increasing the final active agent:lipid ratio resulting in the high ratio active agent:lipid complex of the instant invention. Utilizing the foregoing method and rigid lipids, entrapment or association of up to about 60 or 70% of the initial active agent such as cephalosporin may be obtained compared to the entrapment or association of about one-half that amount without the instant method. Furthermore the final active agent:lipid ratio in the case of cephapirin has increased from about 1:7 (w/w) (cephapirin, egg phosphatidylcholine, and MPV method) to about to better than about 1:1 including about 1.2:1.

Final iodine:lipid ratios for contrast agents are reported for iopamidol C. Musu, et al., *Invest. Radiol.* 23(Supp.1): S126–129 (1988).

By the method of this invention ratios at least of about 2:1 (Iodine weight/weight) or about 4:1 (Iodine w/w), 6:1 (Iodine w/w) and up to even about 8:1 (Iodine w/w) are obtained. 8:1 diatrizoate:lipid complex was prepared. With iodine contrast agents the the use of rigid lipids is advantageous as is the use of unsaturated phosphatidylcholines. It is believed that rigid lipids yield complexes more stable in sera whereas unsaturated phosphatidylcholines yield higher iodine:lipid ratios in complex.

The bench mark in obtaining X-ray contrast with iodinated agents is the amount of iodine delivered. For diatrizoate the iodine to diatrizoate ratio is 1 gram of iodine for 1.623 grams of diatrizoate. In many applications administration of from about 500 to about 1000 mg of iodine per kilogram body weight is required. However depending on various factors such as the concentration of iodine at the site of imaging or the excretion of contrast agent prior to biological availability dosages outside these limits may be utilized. Without being bound by any theory it is thought that since particulates such as liposomes and the complexes of this invention are phagocytosed by liver cells the intracellular space is labeled preferentially to the interstitial space. As will be seen below the contrast agent as disposed by the complexes of this invention facilitate the visualization of liver tumors in particular.

Figure 5A:
FIG. 5 shows freeze-fracture electron micrographs of cephapirin-egg phosphatidylcholine complexes made by either a standard or modified MPV process in which (a) the drug-lipid film was dried to apparent dryness (standard process) or (b) the drug-lipid film followed increased initial aqueous component and maintained residual water—which may contain some residual organic solvent (modified MPV process).
Figure 5B:
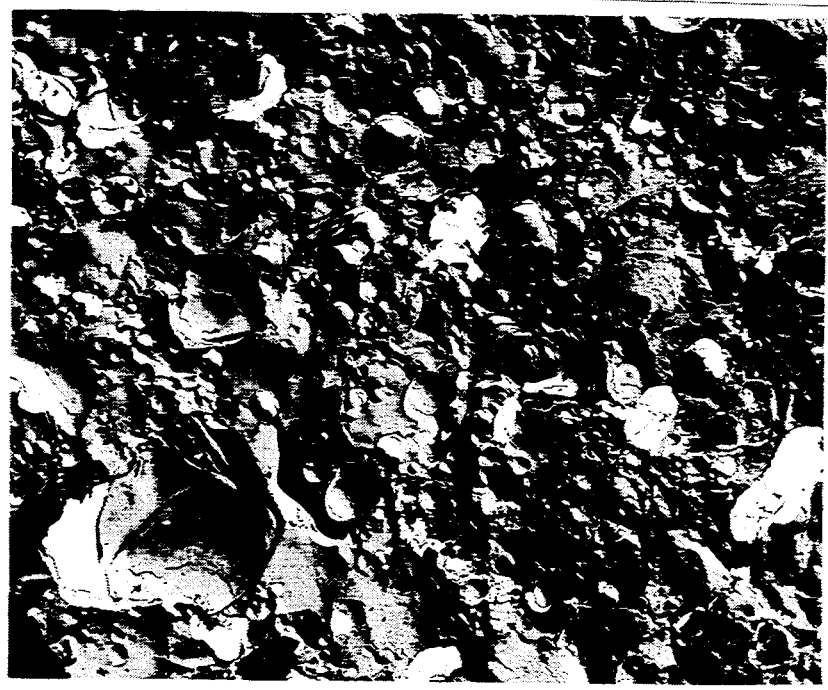

FIGS. 5A and 5B are a freeze-fracture electron micrographs of cephapirin-egg phosphatidylcholine complexes made by either a standard or modified MPV process in which (a) the cephalosporin-lipid film was dried to apparent dryness (standard process) or (b) the cephalosporin-lipid film followed increased initial aqueous component and maintained residual water (modified MPV process). The complexes in (a) appear irregular and distinct from known cephalosporin:lipid complexes, while in (b) the complexes appear to be typical EPC MPVs. Without being bound by any particular theory it appears that as the conventional MPV process entails removing all liquid from the aqueous drug-lipid-organic solvent such removal should be avoided Water removal to dryness results in low drug entrapment and low ratio cephalosporin:lipid complex as in FIG. 5A. By maintaining a residual aqueous phase the entrapment or association roughly doubled, forming the complexes of FIG. 5B.

Figure 6:
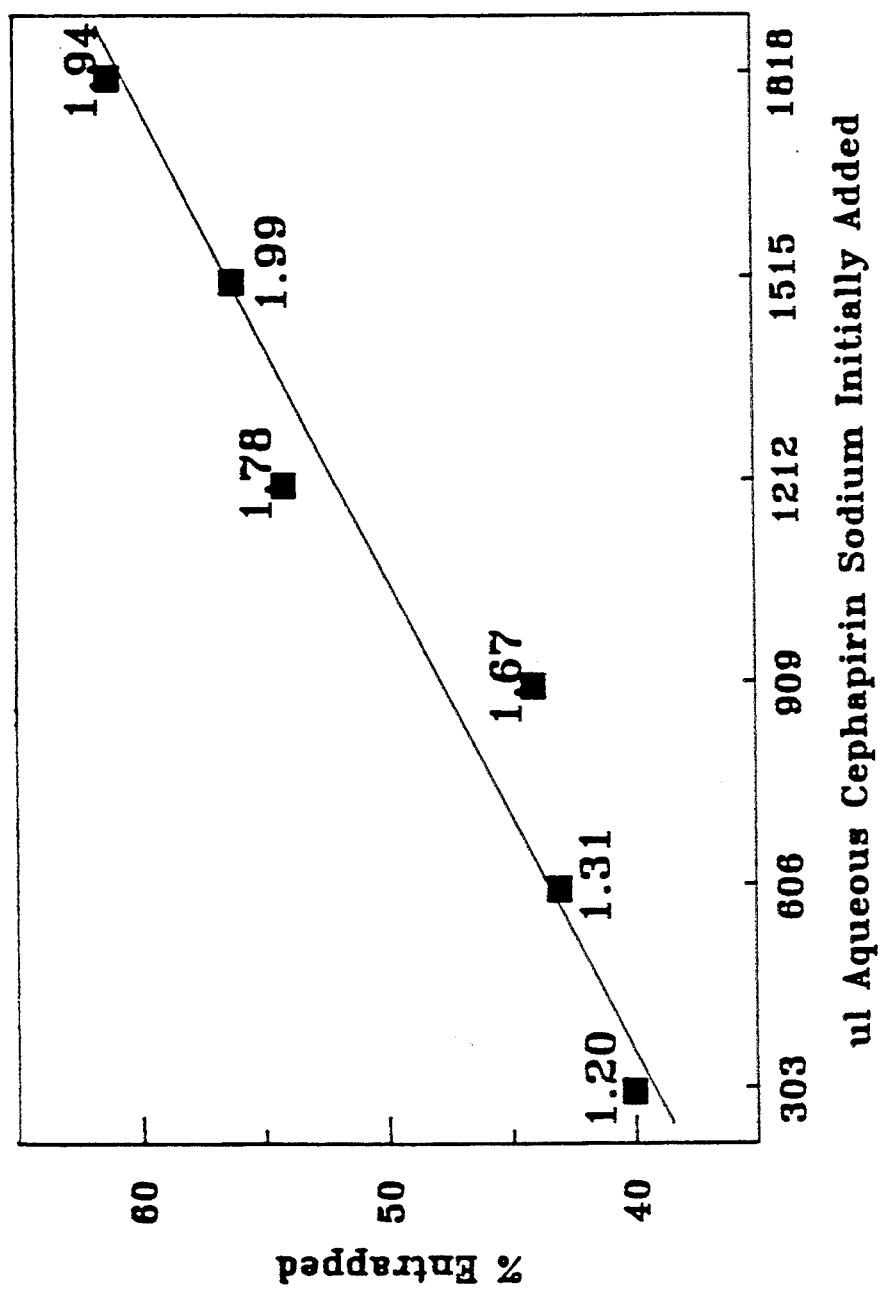
FIG. 6 shows the effect of initial aqueous volume in cephalosporin:lipid mixture on association of cephapirin with dipalmitoylphosphatidylcholine. Data points refer to the final drug:lipid ratios in the washed pellet.
Figure 7:
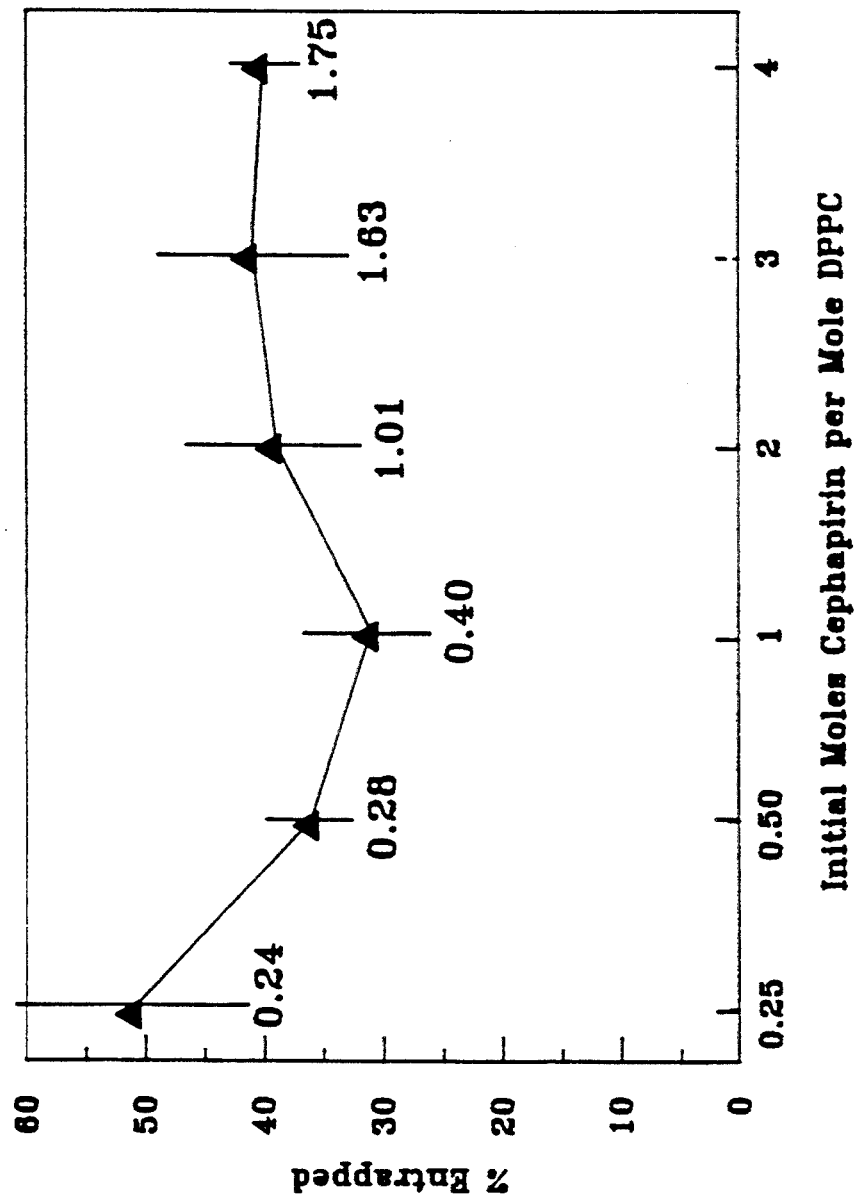
FIG. 7 shows the effect of increasing lipid:cephapirin molar ratio on association of cephapirin with dipalmitoylphosphatidylcholine.

FIG. 6 shows the effect of increasing initial aqueous volume on the entrapment or association of cephapirin in DPPC complex while holding the cephalosporin:lipid constant at 1:3. FIG. 6 discloses that increasing the initial aqueous volume by 6-fold increases from about 1:1 to 2:1 the cephalosporin:lipid ratio. In order to eliminate the possibility that this increase in cephalosporin:lipid ratio was not solely due to increase in aqueous volume rather than a decrease in drug concentration entrapment using the highest aqueous volume tested in FIG. 1 was tested while holding constant this volume as well as lipid amount. FIG. 7 represents the results of a test of entrapment while holding volume and lipid constant. FIG. 7 discloses that no dramatic change in entrapment as the initial cephalosporin:lipid ratio is increased, i.e., more drug added.

The preferred process of the instant invention differs from the MPV process in several ways. First, the initial combination of drug and lipid in a solvent system may not consist of a monophase. However the solvent system passes through a monophase at some point during solvent removal in order to achieve high entrapment or association and result in high active agent:lipid ratio. Regardless of the system used both active agent (also termed drug) and lipid should be completely dissolved in their respective phases. When the active agent is a contrast agent and the lipid a rigid lipid, temperatures about 10° C. above the transition temperature of the lipid are useful. Next, an evaporative procedure such as positive pressure should be used rather than vacuum rotary evaporation in order to limit the loss of water during the solvent removal process. Using a paddle stirrer during this step is advantageous. In the preferred process the rate of solvent removal is monitored so as to avoid solvent removal which is too rapid to permit formation of a distinct monophase. This rate is closely associated with temperature in that higher temperature results in faster solvent removal. It is also desirable to remove greatest amount of organic solvent while retaining the greatest amount of water.

While a number of organic solvents are acceptable in the MPV process, in the instant process combinations of solvents must cosolubilize both drug and lipid and form a monophase during the process. Ethanol is substantially the preferred aqueous miscible organic solvent for high entrapment or association and high ratio active agent:lipid complex. An advantage of ethanol as the aqueous miscible organic solvent is that in vivo high residuals of ethanol do not appear to have deleterious effect on the complex as judged by mouse I.V. pharmacokinetic experiments.

One aspect of this invention is bacterial infection prophylaxis in an animal by maintaining, over an extended period, an available drug level of at least about an MIC level of a cephalosporin in an animal comprising the step of administering to said animal a lipid:cephalosporin complex and preferably a high ratio complex in an increased administration-interval regimen.

The "extended period" for maintenance of prophylactic levels ($T_t$ or $T_p$) of a particular cephalosporin (or other antibacterial or anti-infective) shall be understood to mean a period in excess of at least about twice that time period over which a drug level is about equal to or exceeding an $MIC_p$ or $MIC_t$ that may be maintained by a single administration of an equivalent weight of a free—that is non-complex—form of such cephalosporin.

"Available" as referring to the the prophylactically effective level of a cephalosporin (or other antibacterial or anti-infective) shall be understood to mean bioavailable; that is the cephalosporin, whether in a physiological liquid such as cerebro-spinal fluid, serum, or plasma or in tissue, exhibiting antibacterial activity against pathogens as such pathogens which are presented in vivo.

"Drug level of at least a minimum inhibitory concentration" shall be understood to mean a bacterial infection prophylactic level of cephalosporin (or other antibacterial or anti-infective) sufficient to prevent the proliferation an organism in a subject animal. This bacterial infection prophylactic level will be at least about the MIC level. This level is easily determined by a number of in vitro tests of MIC well known to those skilled in the art. The administered dose to establish in vivo such a prophylactically effective level will vary with the absolute drug level to be obtained, the particular drug, the site where the level is to be established and other factors known to those skilled in the art. For animals, including humans, in the prophylaxis of bacterial infection, the prescribing medical professional will ultimately determine the appropriate dosage for a given subject, and this can be expected to vary according to the age, weight, and response of the animal, route of administration as well as the nature and severity of the bacterial challenge. The prophylactic level and hence dosage amount thereby required in liposome-encapsulated form will generally be about that employed for the free therapeutic agent. In some cases, however, it may be necessary to administer doses outside these limits to establish the desired in vivo drug levels. In a specific application such as the prophylaxis of bacteremia, that is a bacterial infection of the blood, a prophylactic level of cephalosporin shall be understood to mean that level that prevents proliferation of the subject bacteria in the blood.

Cephalosporin shall be understood to mean any member of the cephalosporin class of $\beta$-lactam antibiotics, including, without limitation, cefazolin, cephapirin, cefaclor, cephaloridine, cephoxazole, cefoxitin, cephaloridine, cephradine, cephlexin, cephaloglycine, cefuroxime, cefmenoxime, and cephalothin and analogues and derivatives thereof.

"Iodinated contrast agents" shall be understood to mean iodinated pharmaceutically acceptable materials with discernable X-ray opacity such as without limitation diatrizoate, iocetamic acids, iodamide, iodoximate, iohexol, iopamide, iopamidol, iopanoic acid, iophendylate, iothalamate, iothalamic acid, ipodate calcium, ipodate sodium, metrizamide or tyropanate and which will be understood to include salts thereof such as meglumine (e.g., diatrizoate meglumine, iodamide meglumine, iodoximate meglumine, iopamide meglumine, iothalamate meglumine) as well as other pharmaceutically acceptable salts and additionally analogues and derivatives thereof.

A free drug may be administered to an animal in an amount sufficient to establish an MIC in the animal, generally throughout the animal or at a site within the animal. The MIC for such drug will be present for a certain amount of time specific to each drug and animal and other well known factors. After a time the drug level will fall below the MIC and the drug must be readministered to reestablish the MIC. Thus to continuously maintain a drug level of at least about an MIC, or any given drug level, repeated administrations of the drug must be made to the animal.

Cephalosporin:lipid complex and particularly high ratio cephalosporin:lipid complex is useful in continuously maintaining a drug level of at least an MIC without repeated administrations of drug as compared to free drug. "Cephalosporin:lipid complex" refers to a cephalosporin, associated with a lipid, preferably a rigid lipid. Drug may be adsorbed to the outer surface of a complex or within an aqueous or lipid portion of a complex. As cephalosporin is generally hydrophilic most cephalosporin of a cephalosporin:lipid complex will be within the complex, but this is not critical.

While it is not a limitation of the invention, complexes may be washed to remove active agent such as cephalosporin that is disassociatable from the complex. Since some external cephalosporin is easily separated from the complex upon administration to an animal, it may behave more as free cephalosporin than high ratio cephalosporin:lipid complex. To maximize the complexed dose of cephalosporin while avoiding unnecessary toxicity from disassociatable cephalosporin, in the preferred embodiment, complexes are washed to remove at least about 90% of the disassociatable cephalosporin. Methods of washing complexes are well known in the art and include centrifugation as well as chromatography.

In the practice of this invention for prophylaxis the number of such administrations of drug which is complexed is reduced as compared to free drug that must be administered in equivalent dosage amounts to maintain the same drug level or MIC of drug. The reduction in the number of times a drug must be administered to maintain a given tissue or blood level is necessarily reflected in an increased time interval between administrations of such drug. This is particularly advantageous in prophylaxis of infections that have a lengthy period of intracellular survival including disseminated infections involving the reticulo-endothelial system ("RES") such as *Salmonella sp.* or *Mycobacterium sp.* particularly *Mycobacterium avium intracellulare*. The "increased administration-interval regimen" of this invention shall be understood to mean an administration regimen having an interval between administrations of drug of at least two times that interval at which free drug must be readministered (at equivalent weights and the same drug) to maintain a given drug level. In some therapeutic situations only a single administration of cephalosporin:lipid complex will be required to replace two or more administrations of non-complex drug—which is essentially an infinite increase in the administration-interval and understood to be within this definition. In treatment of disseminated bacterial infections involving the reticulo-endothelial system the persistence of cephalosporin after administration in cephalosporin:lipid complex form permits efficacy where previously cephalosporin therapy had been ineffective.

"Minimum Inhibitory Concentration" ("MIC") is a term well known in the art refering to the least level of a therapeutic agent, usually expressed as w/w or w/v, which will inhibit the proliferation of a pathogen—here a bacterium. As used herein the MIC as detected in blood plasma or serum is termed "$MIC_p$," and understood to refer to a concentration of therapeutic agent in the plasma or serum equal to or greater than the minimum inhibitory concentration of pharmaceutical agent in weight per volume of plasma or serum as determined in vitro for the challenging organism. For cefazolin the $MIC_p$ for many susceptible organisms is about 0.5 ug (base weight)/ml (plasma or serum). Cephalosporin:lipid complex cefazolin may be administered to reach this level and further may reach levels of 10 or 100 ug/ml or more. Base weight will be used to refer to the weight of the active moiety without including the counterion.

As used herein the MIC as detected in tissue is termed "$MIC_t$," and understood to refer to a concentration of therapeutic agent in the tissue equal to or greater than the minimum inhibitory concentration of pharmaceutical agent in weight per weight as determined in vitro for the challenging organism. For cefazolin the $MIC_t$ for many susceptible organisms is about 0.5 ug (base weight)/mg (spleen). Drug:lipid complex cefazolin may be administered to reach this level and further may reach levels of 10 or 100 ug/ml or more.

In the treatment of pathological conditions, the establishing of a prophylactic level of pharmaceutical agent in tissue can also be an effective therapeutic option. Often levels of about 4 or about 8 times the MIC are desired for the most reliable prophylaxis. Such levels are obtainable by the method of the instant invention. Parenteral, such as intravenous, administration of lipid complex pharmaceutical agent such as a cephalosporin results in the prolonged presence of pharmaceutical agent in selected tissue exhibiting pronounced antibacterial activity (Table 1). Experiments show that the tissue levels of cephapirin persist longer than serum or plasma levels and are above the MIC's of most sensitive organisms for an extended period of time, $T_t$. For example, levels greater than about 60 ug/gm are present in the spleen for at least about 24 hours, and in the liver for about 24 hours.

Beyond the prophylactic treatment for bacterial infection, the persistence of high ratio cephalosporin complex is particularly important in the treatment of facultative bacterial intracellular infections also termed disseminated bacterial infections involving the reticuloendothelial system. Facultative refers to pathogens which are capable of surviving inside eukaryotic cells, especially the macrophages of the RES, as well as on an acellular medium. Examples of facultative intracellular organisms are *Listeria monocytogenes, Brucella sp. Legionella pneumophilia, Mycobacterium sp.* and *Salmonella sp*. An additional group of bacterial pathogens, the obligate intracellular organisms, will be included with the facultative organisms. The obligate intracellular organisms, such as coxiella burnetii, can only survive intracellularly.

It will be understood that some bacteria are cephalosporin resistant at subtoxic levels of cephalosporin or sensitive to cephalosporin only at toxic levels. Similar resistance may occur with other antibacterial or anti-infective agents. Those skilled in the art recognize that this invention will be applicable to organisms sensitive to cephalosporin or other antibacterial or anti-infective agents. This is determinable by in vitro testing. Organisms such as *Salmonella sp*. not typically treated with cephalosporin but sensitive in vitro are effectively treated by the instant method.

Prophylactic treatment of bacterial infection is accomplished by the administration of an effective amount of high ratio cephalosporin:lipid complex (or other antibacterial or anti-infective agents). A bacterial infection prophylaxis effective amount will be understood to mean a sufficient amount to achieve the prophylactic response over the desired interval. The bacterial infection prophylaxis effective amount of a given cephalosporin (or other antibacterial or anti-infective agents) will vary with the mode of the administration, the particularities of the recipient, the sensitivity of the target bacteria, and other factors well known in the art.

The duration of prophylaxis from a single dose of cephalosporin:lipid complex (or other antibacterial or anti-infective agents) will vary depending on the specific drug, the animal being treated, the challenging organism, and other factors known to those skilled in the art. In general, a prophylactic tissue level of drug, arising from a single administration of drug, will be maintained in the spleen and liver substantially longer and greater than the $T_t$ of the free agent in similar tissue from a single administration. In the liver the complex persisted at least about 2 times and up to about 5 times or more longer than the free drug. In the spleen free drug was below detectable levels whereas the complex drug lasted at least about 24 hours.

The duration required for prophylactic treatment will vary with the condition of the subject animal. In immunocompromised animals prophylaxis is potentially required for the period of immunocompromise. Thus in acquired immunodeficiency (AIDS) subjects the period may be for life while in subjects suffering neutropenia secondary to chemotherapy or immunosuppressed for organ transplant receipt the period of prophylaxis may be more circumscribed. The duration of such periods of prophylactic need is well known to those skilled in the art.

The maintenance of at least a minimum inhibitory concentration of antibiotic in certain organs of the RES in the absence of detectable serum levels may be advantageous for the prevention and treatment of bacteremia in patients at risk or in the treatment or suppression of certain chronic infections (e.g., osteomyelitis, mycobacterium avium intracellulare infection, *Salmonella sp.* infections).

The reticulo-endothelial system or RES is understood to refer to cells of the body having both endothelial and reticular attributes and showing a common phagocytic behavior toward dyestuffs. Such cells tend to incorporate administered cephalosporin:lipid complex. Included cells are those of the spleen and lymph nodes, Kupffer cells of the liver, alveolar macrophages of the lung, the reticulo-endothelium of bone marrow and the clasmatocytes. In the terminology of this invention bone the marrow and hard tissue will be deemed to be within the RES, and bacterial osteomyelitis to be an infection of the RES.

To determine the bioavailability of cefazolin when administered in a cephalosporin:lipid complex, several infection models were studied.

In general, the serum level and tissue distribution studies for antibiotics were performed in mice by injecting a single intravenous dose of free or encapsulated antibiotic and quantitating the amount of antibacterial activity in the serum or plasma and selected tissues of the animals at intervals thereafter.

The antibacterial activity was measured by an agar well diffusion bioassay, though other assays for antibacterial activity or chemical, or immunological assays for the drug substance are known to those skilled in the art. Briefly, the agar well diffusion bioassay used here were performed by cutting wells into an agar such as Trypticase Soy Agar (Difco., Detroit, Mich.) that were previously seeded with a test bacteria such as *Bacillus subtilis* (ATCC #6633). The wells were filled with a small amount of test material here about 50 ul of the test sample, and the agar plates were incubated. *Bacillus subtilis* incubation was for about 16–24 hours at about 35° C. Growth of a bacterial "lawn" around the well was inhibited by antibiotic present in the agar as diffused from the test sample. The diameters of the zones of inhibited growth around the wells were proportional to the concentration of antibiotic in the test sample and were quantitated by comparison with known, standard antibiotic solutions.

The administration (parenteral) to an animal of a cephalosporin:lipid complex antibiotic such as cefazolin to an animal characteristically resulted in a higher peak serum or plasma level as measured by the concentration of pharmaceutical agent in the plasma at time zero (Cpo) than was observed for the pharmaceutical agent in the free form. Also observed was a longer serum or plasma half-life (T ½) for the cephalosporin:lipid complex form than for the free form, and a greater area under a graphic plot of serum or plasma concentration vs time, termed area under curve (AUG).

Figure 8:
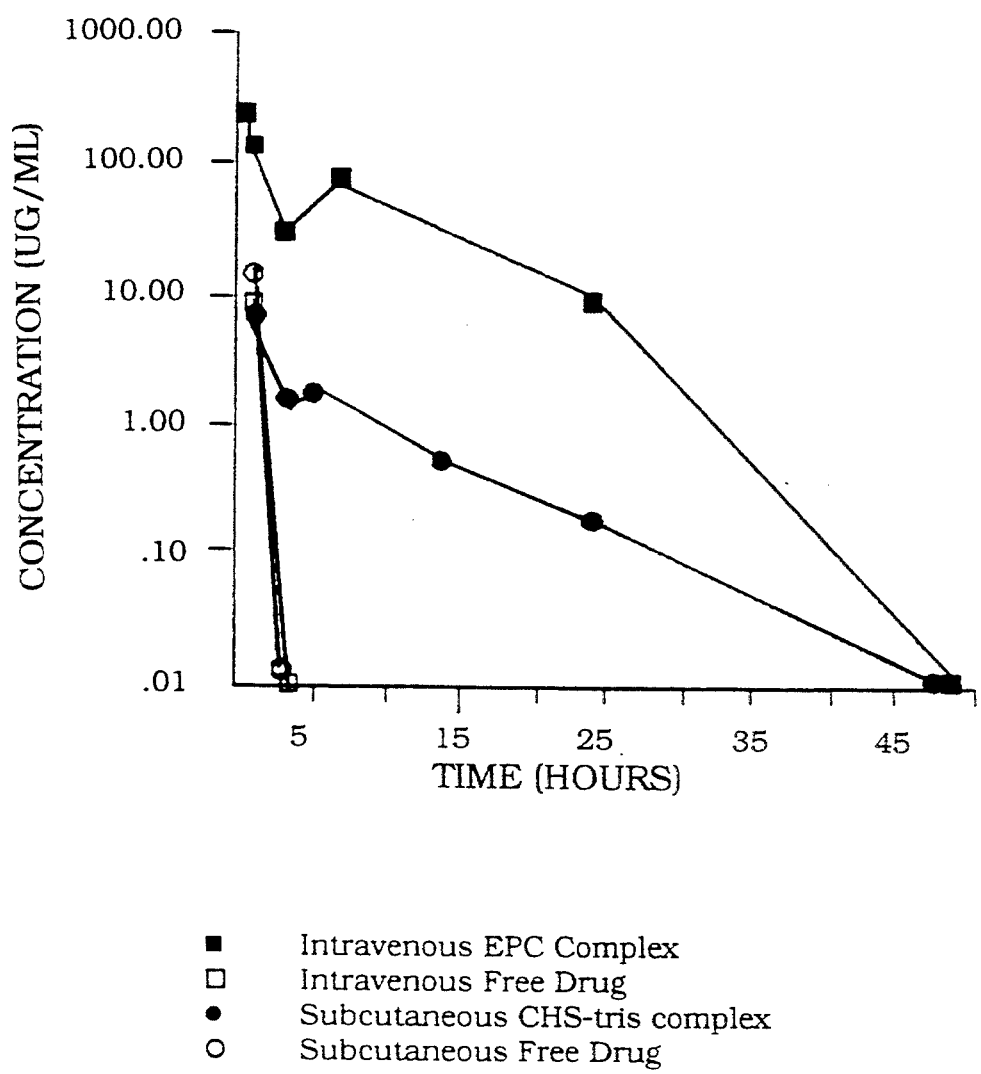
FIG. 8 shows serum levels of cephapirin activity in mice at intervals after injection of free cephapirin in the form of cephalosporin:lipid complex cephapirin in a single dose of 200 mg/kg. Each point represents the means of 3-5 mice.
Figure 9:
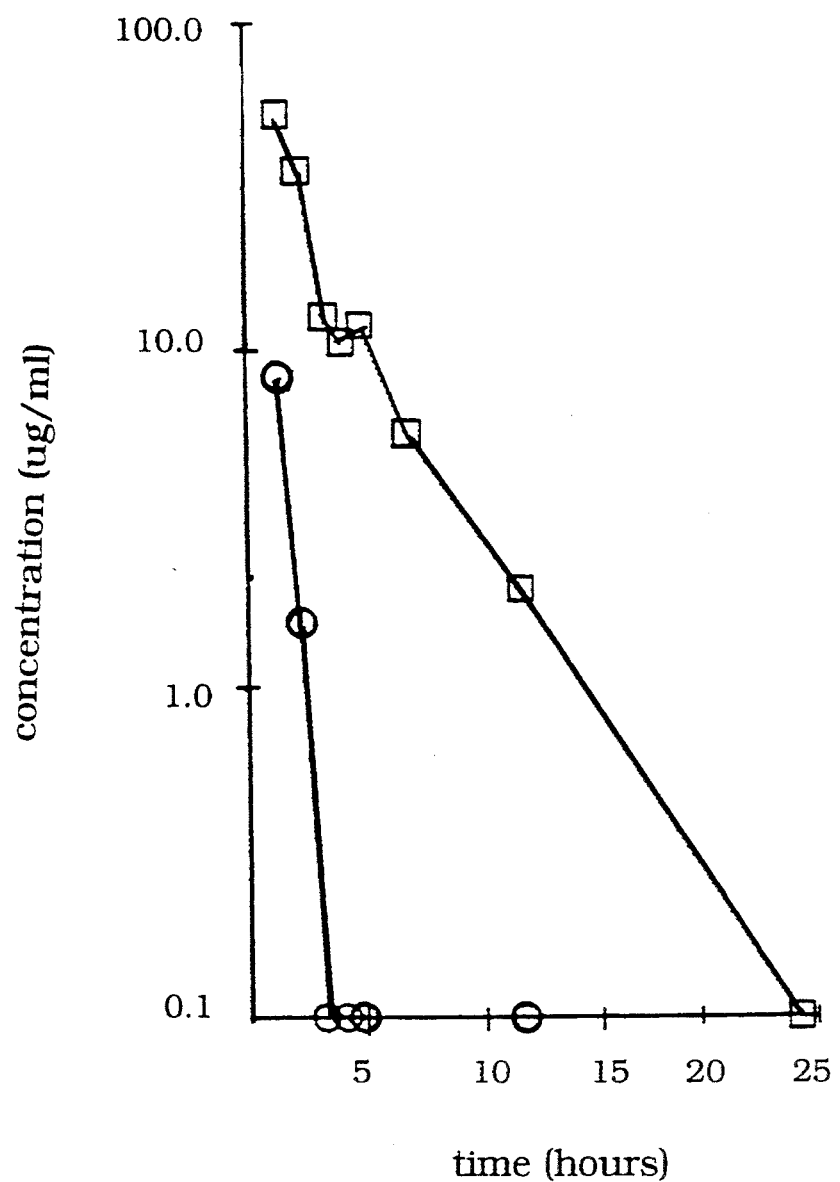
FIG. 9 shows mean serum levels of cefazolin activity in mice at intervals after a single intravenous dose of 100 mg/kg of free cephapirin or cephalosporin:lipid complex cephazolin composed of DPPC, with a final drug to lipid ratio of 1.5 by weight.

FIG. 8 shows serum levels of cephapirin activity in mice at intervals after injection of free cephapirin of cephalosporin:lipid complex cephapirin (each, 200 mg/kg), while FIG. 9 shows cefazolin activity (each, 100 mg/kg). Both cephapirin and cefazolin display prolonged activity in serum and activity at a higher level by the cephalosporin:lipid complex preparation as compared to the free drug. It can be seen that in both FIG. 8 and FIG. 9, the cephapirin/cefazolin level and hence activity in the serum or plasma was greater and more prolonged with the cephalosporin:lipid dosage form when compared to the free drug. Extended prophylactic activity in the serum can also be achieved by subcutaneous administration of a cephalosporin:lipid complex antibiotic.

Figure 12:
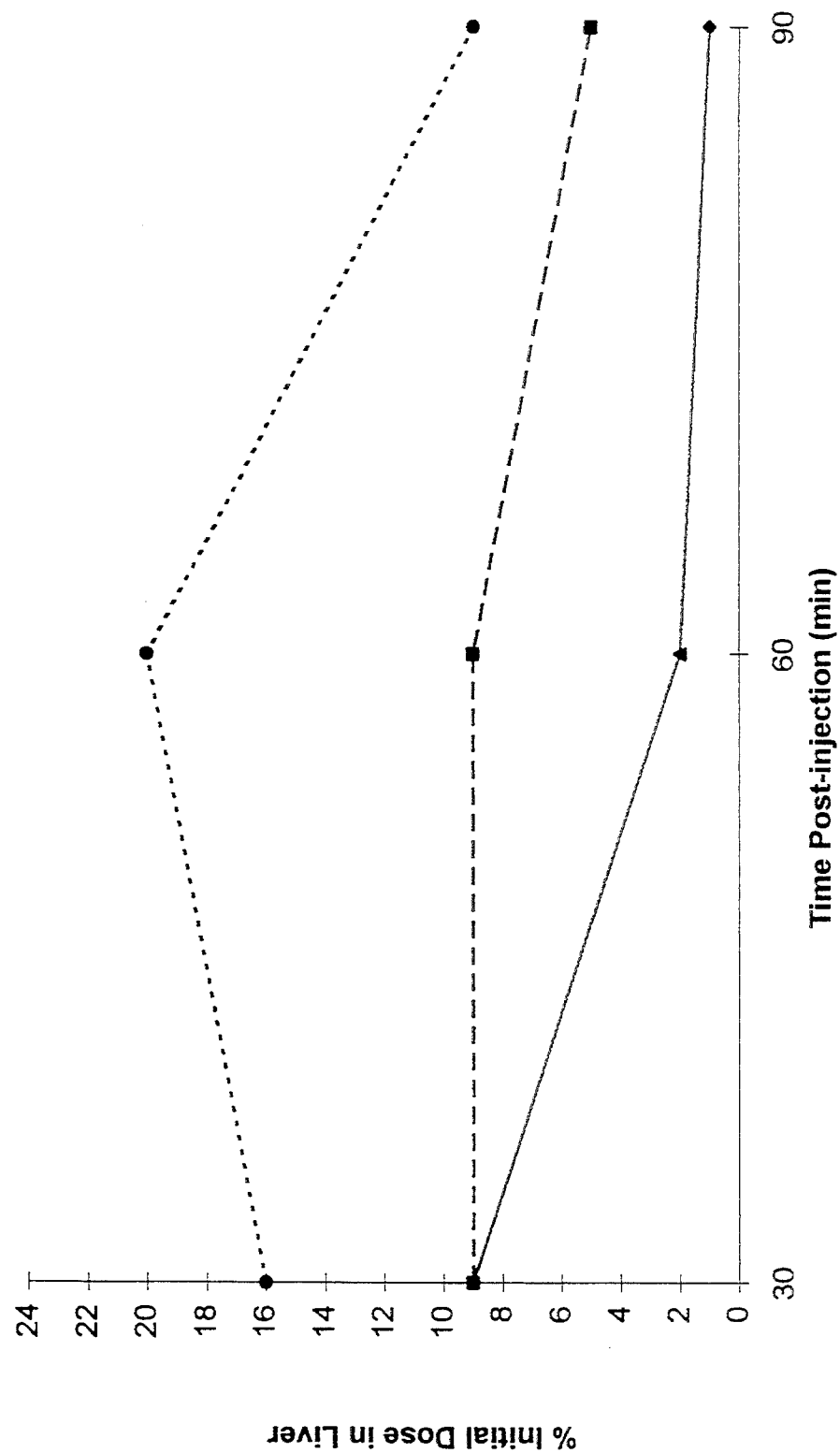
FIG. 12 discloses the retention of contrast agent in the liver in high ratio complex form using DPPC-diatrizoate MPVs, versus free contrast agent, using aqueous diatrizoate, as monitored by $^{125}$I-diatrizoate.

Contrast agents were tested in mice by injecting a single intravenous dose of free or complexed contrast agent (diatrizoate) via the tail vein. The final iodine/lipid ratio in the MPVs was 4.5:1 (w/w); the iodine concentration was 8.5 mg/ml and the lipid concentration was 3.5 mg/ml. The specific activity of the doses were ~10000 c/mg I. At a dose of 924 mg/kg iodine the level of greater than about 2 mgs I per gram of liver was achieved. (FIG. 12). See Table 1 below.

TABLE 1

| mg I Dosed | mg/kg Iodine | mg lipid Dosed | mg/kg Lipid | mg I/g Liver | | |
|---|---|---|---|---|---|---|
| | | | | 30' | 60' | 90' |
| 15.4 | 616 | 3.4 | 136 | 1.3 | 1.0 | 0.7 |
| 23.1 | 924 | 5.1 | 204 | 3.0 | 3.2 | 1.6 |
| 23.1 | 924 | — | — | 2.8 | 0.8 | 0.3 |

The final iodine/lipid ratio in the MPVs was 4.5:1 (w/w); the iodine concentration was 8.5 mg/ml and the lipid concentration was 3.5 mg/ml. The specific activity of the doses were ~10000 c/mg I. The efficacy of prophylactic use of antibiotics may be tested by a number of methods well known to those skilled in the art. Several models for prophylactic efficacy testing are briefly described below.

Staphylococcal Abscess Model

*S. aureus* (ATCC #29740) was grown overnight at 30° C. in trypticase soy broth. Aliquots of this suspension were frozen at −70° C. The in vitro minimal inhibitory concentration (MIC) of cephapirin sodium for this strain was shown to be 0.05–0.10 ug/ml by the microtiter dilution method. For use, cultures were thawed and diluted with saline to contain the desired number of colony forming units (CFU) per ml. Mice (out-bred CD-1 males) were injected subcutaneously with 0.1 ml of *S. aureus* suspension in the abdominal area. Treatment with free or encapsulated drug was given before or after infection. At four days after infection, mice were killed by cervical dislocation, the abscesses were carefully dissected out and their diameters measured.

Staphylococcal Septicemia Model

The *S. aureus* inoculum was prepared as for the abscess model. Mice were inoculated intraperitoneally with $2 \times 10^8$ CFU in 5% hog mucin. Treatment was given before or after infection. Mortality was monitored for 3 days post-infection.

Salmonella typhimurium Septicemia Model

*S. typhimurium* (ATCC #14028) was grown in trypticase soy broth at 35° C. overnight. Aliquots of this suspension were frozen and maintained at −70° C. For use, cultures were thawed and diluted to contain 700 CFU/ml in 0.9% saline. Mice were inoculated intravenously (0.1 ml) via the lateral tail vein. Treatment was given at various times after infection. Mortality was monitored daily for two weeks.

In addition to providing prolonged serum antibacterial activity levels, the EPC liposome formulation targets the drug to particular organs when given intravenously. This particularly includes the reticulo-endothelial system and most particularly the spleen.

*Salmonella typhimurium* is a facultative intracellular bacterium capable of causing systemic infection in mice. Spontaneous mouse salmonellosis usually results from ingestion of the organism (via contaminated feed, bedding or feces). Infection can also occur by a conjunctival route or after experimental sub-cutaneous, intraperitoneal or intravenous inoculation. In all cases, the organism gains access to the systemic circulation causing a septicemia followed by localization with the major reticulo-endothelial organs (spleen, liver, lymph nodes). The bacteria can survive and multiply within macrophages and will cause a chronic infection unless death intervenes.

The high ratio cephalosporin complex administered to test animals substantially increased survival time at all doses and treatment times examined and exceeded free cephalosporin administration.

Cephalosporin:lipid complex cefazolin provides significant prophylactic activity, a $T_f$ for periods of time that first exceed that of the free pharmaceutical agent. Clearly the high ratio cephalosporin complex was significantly longer acting than the free cephalosporin.

In studies of tissue levels of cephalosporin it has been found that tissue levels of cephalosporin following administration of high ratio cephalosporin complex may exceed plasma levels in both concentration of drug and length of time of drug retention. It is therapeutically effective in prophylaxis for periods of up to seven days or longer as the cephalosporin is bioavailable to stop bacterial proliferation. Therefore loading of an RES organ—a concomitant of high ratio cephalosporin complex administration—such as the spleen with cephalosporin, even in the absence of detectable plasma levels of drug can afford protection against organisms in the blood (e.g., bacteremia)

The method of this invention is affected by complex size in some embodiments. Prophylactic uptake by the RES occurs most rapidly with complexes greater than 0.5 u in diameter. Thus if extended term plasma levels of cephalosporin are the primary objective, this is promoted by using complexes of less than 0.5 u in diameter while RES loading is facilitated by the use of complexes of about 0.5 u or greater. In either situation the RES will ultimately be the repository of much of an administered dose of high ratio cephalosporin complex.

While conventional liposomes are useful for prophylaxis in the practice of this invention including MLVs, small sonicated unilamellar vesicles, large unilamellar vesicles, LUVETs, SPLVs, FATMLVs, steroidal liposomes or alpha-tocopherol based vesicles, the high ratio cephalosporin:lipid complexes are preferred.

In a lipid based drug delivery system, a bioactive agent such as a drug is entrapped in or associated with a lipid such as in a cephalosporin:lipid entity and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,114,179; Lenk et al., U.S. Pat. No. 4,522,803; and Fountain et al., U.S. Pat. No. 4,588,578.

The mode of administration of the active agent:lipid complex may determine the sites and cells in the organism to which the compound will be delivered. Cephalosporin:lipid complex (or other antibacterial or anti-infective agents) can be administered alone but will generally be administered in admixture with a pharmaceutical carrier selected with regard to the intended route of administration and standard pharmaceutical practice. Iodinated contrast agent complex will be similarly administrable. The preparations may be injected parenterally, for example, intra-arterially or intravenously. The preparations may also be administered via oral, subcutaneous, or intramuscular routes, or by inhalation. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art. In some embodiments high ratio cephalosporin:lipid complex cephalosporin may be employed in unit dosage form adapted to convenient administration to a subject animal including a human.

A "therapeutically effective amount" will be understood to mean a sufficient amount to achieve a physical or physiological response The therapeutically effective amount of a given cephalosporin will vary with the mode of the administration, the particularities of the recipient, the sensitivity of the target bacteria, and other factors well known in the art. A therapeutically effective amount of contrast agent will vary with the aspect of the subject to be imaged and with the nature of the X-ray imaging equipment but will be easily determinable by empirical observation by those skilled in the art.

For administration to humans in the curative treatment of disease states or for imaging, the prescribing physician will ultimately determine the appropriate dosage for a given human subject, and this can be expected to vary according to the age, weight, and response of the individual as well as the nature and severity of the patient's disease. The dosage of the drug in cephalosporin:lipid complex form or for iodinated contrast agent:lipid complex will generally be about that employed for the free active agent. In some cases, however, it may be necessary to administer doses outside these limits.

EXAMPLE 1

Preparation of High Ratio Cephalosporin:Lipid Complex

In a 50 ml round-bottom flask, 92 ul of a 300 mg/ml cefazolin sodium stock solution was diluted to 2 mls by adding 1.908 mls dH$_2$O (total 26.2 mgs of drug). 2 mls of 100% ethanol was added along with 2.5 mls of a 20 mg/ml lipid (DPPC) stock solution (total 50 mgs of lipid). The flask was immersed in a 37° C. circulating water bath while a stream of air was used to agitate the resulting mixture. The stream of air was adjusted so that it was strong enough to thoroughly mix and stir the mixture during solvent removal. After 1.5 to 2 minutes the mixture changed from a dispersed biphase (cloudy) to a monophase (clear). As solvent removal continued the mixture became opaque and gelatinous or gel-like. The gel state indicated continued hydration. The purging was continued for 5 minutes at which time only a very faint odor of ethanol was detected. At this point the cephalosporin:lipid:aqueous mixture was thick and somewhat gelatinous. The mixture was briefly heated in a 51° C. circulating water bath until the mixture liquified; this required about 5 seconds. The mixture was then transferred to 2.5-ml conical microfuge tubes and spun at 15000 rpm in the microfuge for 10–15 minutes forming a cephalosporin:lipid complex pellet. The aqueous phase was removed from above the pellet and 145 mM saline was added to fill the tube. The tube was vortexed briefly until the pellet was thoroughly resuspended. The cephalosporin:lipid complex was recentrifuged and resuspended as above. The resulting cephalosporin:lipid complex was washed two more times either as described above or may be combined with other materials including other batches of cephalosporin:lipid complex for subsequent washing. If the complexes are to be combined, each was transferred to a single Corex TM tube (Corning Glass Works, Corning, N.Y.) after the first resuspension and spun at 10000 g for 10–15 minutes. The supernatant was removed from the pellet and the pellet was resuspended in saline as described above. The washed pellet was assayed for drug, lipid and residual ethanol. The results of such tests disclosed 18.1 mg drug/ml, 32.3 mg/ml lipid and 2% residual alcohol.

EXAMPLE 2

Preparation of High Ratio Cephalosporin:Lipid Complex

In a 50 ml round-bottom flask, 217 ul of a 300 mg/ml cefazolin sodium stock solution was diluted to 2 mls by adding 1.783 mls dH$_2$O (total 65.1 mg of drug). 2 mls of 100% ethanol was added along with 2.5 mls of a 20 mg/ml lipid (DPPC) stock solution (total 50 mgs of lipid). The flask was immersed in a 37° C. circulating water bath while a stream of air was used to agitate the resulting mixture. The stream of air adjusted so that it was strong enough to thoroughly mix and stir the mixture during solvent removal. After 1.5 to 2 minutes the mixture changed from a dispersed biphase (cloudy) to a monophase (clear). As solvent removal continued the mixture became opaque and gelatinous or gel-like. The gel state indicated continued hydration. The purging was continued for 5 minutes at which time only a very faint odor of ethanol was detected. At this point the cephalosporin:lipid:aqueous mixture was thick and somewhat gelatinous. The mixture was briefly heated in a 51° C. circulating water bath until the mixture liquifies; this required about 15 seconds. The mixture was then transferred to 2-1.5 ml conical microfuge tubes and spun at 15000 rpm in the microfuge for 10–15 minutes forming a cephalosporin:lipid complex pellet. The aqueous phase was removed from above the pellet and 145 mM saline was added to fill the tube. The tube was vortexed briefly until the pellet was thoroughly resuspended. The cephalosporin:lipid complex was recentrifuged and resuspended as above. The resulting cephalosporin:lipid complex was washed two more times either as described above or may be combined with other materials including other batches of cephalosporin:lipid complex for subsequent washing. If the complexes are to be combined, each was transferred to a single Corex TM tube (Corning Glass Works, Corning, N.Y.) after the first resuspension and spun at 10000 g for 10–15 minutes. The supernatant was removed from the pellet and the pellet was resuspended in saline as described above. The washed pellet was assayed for drug, lipid and residual ethanol. The results of such tests disclosed 11.5 mg drug/ml, 14.9 mg lipid/ml and 2% residual alcohol. The trapping efficiency of the cephalosporin was 74% and the final cephalosporin:lipid ratio was 0.77:1.

EXAMPLE 3

Preparation of High Ratio Cephalosporin:Lipid Complex

In a 50 ml round-bottom flask, 434 ul of a 300 mg/ml cefazolin sodium stock solution was diluted to 2 mls by adding 1,566 mls dH$_2$O (total 130 mg of drug). 2 mls of 100% ethanol was added along with 2.5 mls of a 20 mg/ml lipid (DPPC) stock solution (total 50 mgs of lipid). The flask was immersed in a 37° C. circulating water bath while a stream of air was used to agitate the resulting mixture. The stream of air was adjusted so that it was strong enough to thoroughly mix and stir the mixture during solvent removal. After 1.5 to 2 minutes the mixture changed from a dispersed biphase (cloudy) to a monophase (clear). As solvent removal continued the mixture became opaque and gelatinous or gel-like. The gel state indicated continued hydration. The purging was continued for 5 minutes at which time only a very faint odor of ethanol was detected. At this point the cephalosporin:lipid:aqueous mixture was thick and somewhat gelatinous. The mixture was briefly heated in a 51° C. circulating water bath until the mixture liquifies; this required about 15 seconds. The mixture was then transferred to 2-1.5 ml conical microfuge tubes and spun at 15000 rpm in the microfuge for 10-15 minutes forming a cephalosporin:lipid complex pellet. The aqueous phase was removed from above the pellet and 145 mM saline was added to fill the tube. The tube was vortexed briefly until the pellet was thoroughly resuspended. The cephalosporin:lipid complex was recentrifuged and resuspended as above. The resulting cephalosporin:lipid complex was washed two more times either as described above or may be combined with other materials including other batches of cephalosporin:lipid complex for subsequent washing. If the complexes are to be combined, each was transferred to a single Corex ™ heavy duty glass tube (Corning Glass Works, Corning, N.Y.) after the first resuspension and spun at 10000 g for 10-15 minutes. The supernatant was removed from the pellet and the pellet was resuspended in saline as described above. The washed pellet was assayed for drug, lipid and residual ethanol. The results of such tests disclosed 19 mg drug/ml, 13.9 mg lipid/ml and 2% residual alcohol. The trapping efficiency of the cephalosporin was 60% and the final cephalosporin:lipid ratio was 1.43:1.

EXAMPLE 4

Cephalosporin:Lipid—Preparation 2.5 ml of a 50 mg/ml cephapirin sodium solution was used to disperse and hydrate 200 mg CHS$_{tris}$ with mechanical stirring. After stirring the resulting suspension for 1 minute, the suspension was placed on a rocker for 3 hours at 4° C. The suspension was uniform in appearance and was then diluted to 3 mls with phosphate buffered saline (Mg$^{2+}$ and Ca$^{2+}$ free) at pH 7.4. The final suspension contained 40 mg cephapirin/ml as determined by agar diffusion assay.

EXAMPLE 5

Cephalosporin:Lipid Complex—Preparation 2 g of CHS$_{tris}$ and 1.075 g of cephapirin sodium were weighed out and transferred to a 125 ml Erlenmeyer flask. 20 ml of distilled water was added to the flask and the mixture shaken over night at 4° C. 35 ml phosphate buffered saline (Mg$^{2+}$ and Ca$^{2+}$ free) at pH 7.4 was added to the mixture which was then transferred to 2 30 ml Corex ™ tubes and centrifuged at 10,000 g for 30 minutes. The supernatant was decanted, and the pellet of cephalosporin:lipid complex was resuspended in 20 ml phosphate buffered saline per tube, and the tubes recentrifuged as above. The final pellet volume was 22 ml. The final drug concentration in the pellet was 17.1 mg/ml as measured by agar diffusion assay. The final cephalosporin:lipid ratio was 6:1.

EXAMPLE 6

Cephalosporin:Lipid Complex—Preparation 20 ml of a stock solution of EPC at 100 mg/ml in CHCl$_3$ was diluted to 200 ml with 100% ethanol in a 500 ml round-bottom flask. 1.075 g of cephapirin sodium dissolved in distilled water sufficient for a final volume of 6 ml was added. A clear yellow monophase resulted. The monophase was placed on a rotary evaporator with a 40° C. water bath and pressure of 740 mmHg until the monophase appeared as a dry lipid/drug film and no ethanol odor was detected. Rotary evaporation took 30 minutes ±5. The film was resuspended in 30 ml phosphate buffered saline and transferred to 2 30 ml Corex ™ tubes. The tubes were centrifuged at 10,000 g for 10 minutes. The supernatants were decanted, the pellets resuspended in 10 ml phosphate buffered saline per tube and recentrifuged as above. The final pellets of cephalosporin:lipid complex was 12 ml. The final drug concentration was 15.7 mg/ml by agar diffusion assay and the final cephalosporin:lipid ratio was 11:1 (w/w).

EXAMPLE 7

Cephalosporin:Lipid Complex—Prolonged Serum Activity

Cephapirin activity in the serum of mice was determined at intervals after subcutaneous or intravenous administration of free or complexed drug. FIG. 8 shows the results of a typical experiment. Maximal activity was found in the serum of mice given free cephapirin (by either route) at the earliest time points examined (one half to one hour post-injection). The half-life of free drug was estimated to be approximately 20 minutes for both intravenous and sub-cutaneous administration. For free drug no activity was detectable in the serum at 3 hours or later. Animals given similar doses of unwashed CHS-tris cephapirin (with approximately 30% of the administered dose encapsulated) subcutaneously showed prolonged serum activity with levels of approximately 0.2 ug/ml (0.01% of the original dose) still present at 24 hours post-injection. Mice that received washed EPC complex (where 100% of the administered dose was encapsulated) by the intravenous route also showed prolonged serum activity. With a 200 mg/kg dose, serum levels were 10 ug/ml or greater for 24 hours after injection. In both cephalosporin:lipid complex cases, the apparent half-life of the drug in serum was greater than four hours.

Intravenous administration of 200 mg/kg of free cephapirin resulted in detectable activity in the liver and kidney one hour after injection (Table 2). No activity was detected at 3 hours or later. Mice that received EPC cephalosporin:lipid complex showed activity in the kidney for 24 hours after injection. The spleen and liver showed greatly enhanced activity that persisted for at least 24 hours.

EXAMPLE 8

Cephalosporin:Lipid Complex—Prolonged Serum Activity

Intravenous injection of a single 100 mg/kg dose of free cefazolin dosium in mice results in a mean serum concentration of 8 to 20 ug/ml at one hour post dose (FIG. 9). The serum level declined rapidly to approximately 2 ug/ml at 2 hours and is below the level of detection at 3 hours after administration. In contrast, animals that received the cephalosporin:lipid complex containing the same 100 mg/kg dose of cefazolin showed serum concentrations of 55 to 80 ug/ml at one hour and still had levels of 2 to 3 ug/ml at 12 hours post dose.

EXAMPLE 9

Cephalosporin:Lipid Complex

Prophylaxis of Localized Staphylococcal Infection

Figure 10:
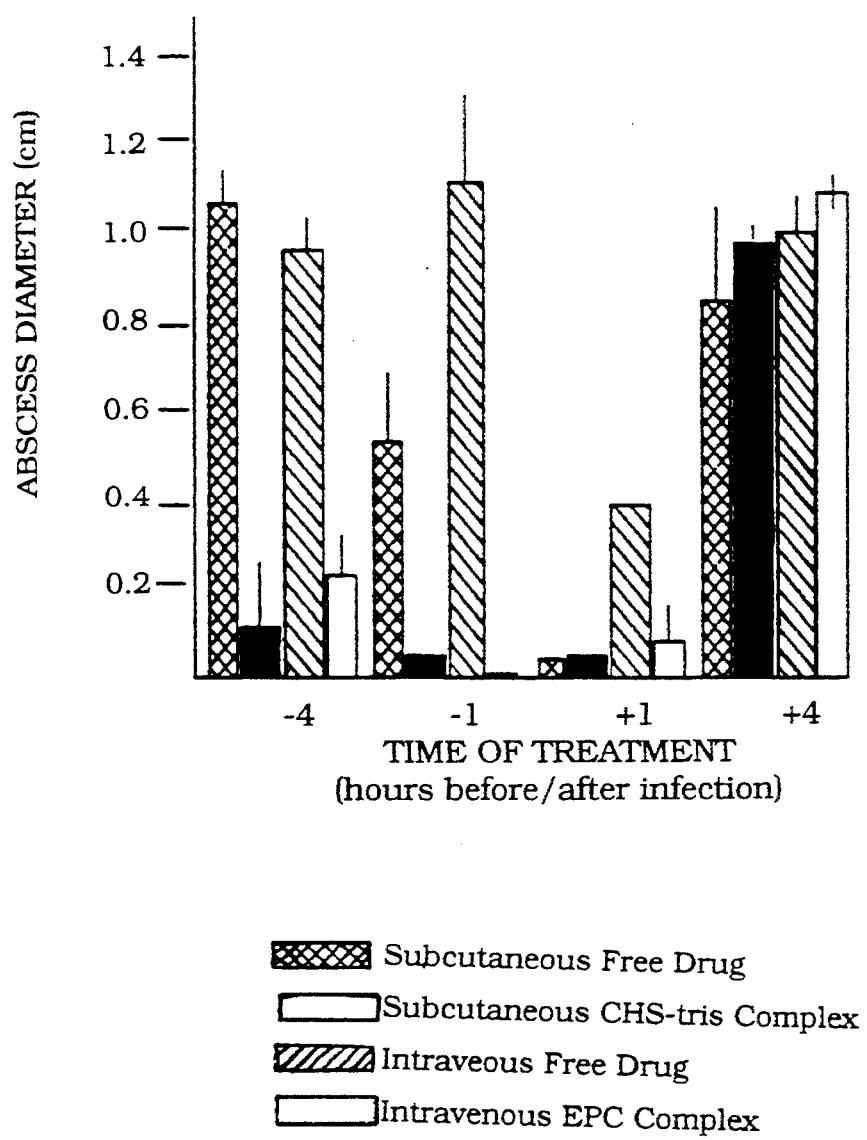
FIG. 10 shows the effect of the time of treatment with a single 200 mg/kg dose of cephapirin, either in free or in cephalosporin:lipid complex, on abscess size in mice. Mean +S.E.M. of 5 mice per group is shown.

To determine the effect of treatment on abscess development, mice were given a single intravenous or subcutaneous injection of free or complexed cephapirin at various times before or after injection. FIG. 10 shows that treatment with free cephapirin (by either route) has no effect on abscess size when given at four hours before infection. Treatment at one hour before infection reduced abscess size slightly while treatment at one hour after infection significantly reduces or prevents abscess development. In contrast, treatment with cephalosporin:lipid complex cephapirin (either iv with EPC complex or sc with CHSt complex) affords significant protection against abscess development when administered up to four hours before infection as well as when given at one hour after infection. Additional investigation found that empty EPC liposomes given iv or empty CHS$_t$ liposomes given sc had no effect on abscess size, and empty EPC liposomes plus free drug gave results similar to free drug alone.

EXAMPLE 10

Cephalosporin:Lipid Complex

Prophylaxis of Systemic Staphylococcal Infection

The effect of free and CHS$_{tris}$ cephalosporin:lipid complex cephapirin was compared in an acute staphylococcus septicemia model. Table 3 shows that 70 to 80% of untreated animals die within 72 hours of infection. Mice treated subcutaneously with free or cephalosporin:lipid complex at one hour before infection survived until the end of the experiment (14 days). Treatment at four hours before infection with cephalosporin:lipid complex protected the majority of mice whereas treatment with free drug at that time had no effect on survival.

EXAMPLE 11

Cephalosporin:Lipid Complex

Therapy of Systemic Salmonellosis

Figure 11:
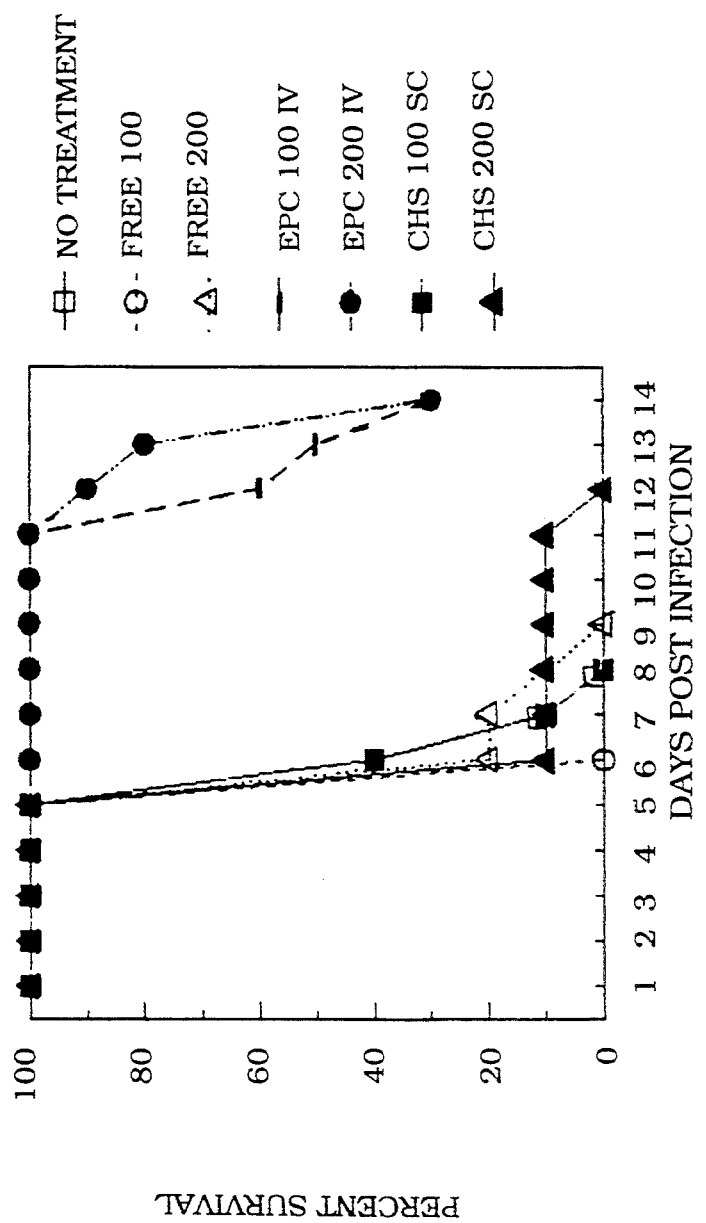
FIG. 11 shows the effect of cephapirin either free or in cephalosporin:lipid complex on mortality of mice after intravenous inoculation of 700 CFU of *Salmonella typhimurium* (10 mice per group). Intravenous administration is abbreviated as "IV" and subcutaneous administration is abbreviated as "SC".

Mice that were inoculated intravenously with 700 CFU of *S. typhimurium* and received no treatment died within 6-8 days after infection (FIG. 11). Treatment on days 2 and 4 post-inoculation with free cephapirin by the subcutaneous or I.V. route did not prolong survival. Intravenous treatment with cephapirin in unwashed stearylamine containing EPC complex enhanced survival. In this case, the cephalosporin:lipid complex preparation was not washed so that 30% of the administered dose was encapsulated.

EXAMPLE 12

Contrast Agent:Lipid Complex—Preparation

Two mls diatrizoate (Renograftn-76 TM, Squibb, Princeton, N.J.) in the form of sodium and meglumine salts at 370 mg/ml was placed in a 100 ml round-bottom flask. To this was added 2 mls of absolute ethanol while mixing followed by addition of 50 mgs of hydrogenated soy phosphatidylcholine in 2.5 ml chloroform. The material in the flask was mixed by swirling the flask vigorously forming an emulsion. The chloroform organic solvent phase was removed by using a stream of nitrogen at a flow rate of between about 5-10 Lpm to stir the material while the flask is immersed in a 30° C. water bath. Solvent removal was continued for 10 minutes. Then 7 mls of 0.9% saline was added to the flask and mixing was accomplished by swirling. The material was then transferred to a 15-ml Corex TM tube and centrifuged at approximately 10,000×g for 15 minutes at 20° C. The supernatant was removed and the pellet resuspended in 10 mls 0.9% saline, and the washing procedure repeated two more times. The resulting contrast agent:lipid complex was found to contain 58.7 mg/ml iodine (94.7 mg/ml diatrizoate) and 20.8 mg/ml phospholipid for a final iodine:lipid ratio of 2.8:1.

TABLE 2

| | Tissue distribution of cephapirin activity after intravenous administration of free or EPC complex formulation | | | | |
|---|---|---|---|---|---|
| | | ANTIBIOTIC ACTIVITY (ug/gm Tissue)[a] | | | | |
| TISSUE | FORMULATION | 1 | 3 | 7 | 10 | 24 |
| KIDNEY | Free | 49 ± 8 | <0.5 | <0.5 | <0.5 | <0.5 |
| | EPC complex | 118 ± 15 | 43 ± 6 | 25 ± 3 | 15 ± 6 | 2 ± 1 |
| SPLEEN | Free | <0.5 | <0.5 | <0.5 | <0.5 | <0.5 |
| | EPC complex | 1202 ± 12 | 1243 ± 305 | 1031 ± 181 | 570 ± 95 | 67 ± 2 |
| LIVER | Free | 46 ± 12 | <0.5 | <0.5 | <0.5 | <0.5 |
| | EPC complex | 171 ± 12 | 228 ± 34 | 143 ± 48 | 149 ± 22 | 66 ± 22 |

[a]Values given are the mean of 3 to 5 mice ± S.E.M.

TABLE 3

Effect of Free and CHS-tris complex Encapuslated Cepharin on Survival of Mice with Acute Staphylococal Septicemia

| TIME OF TREATMENT | DOSE (mg/kg) | % Survival at 72 hours[a] | |
|---|---|---|---|
| | | Free Cephapirin | CHSt Cephapirin |
| 1 hour | 200 | 100 | 90 |
| | 100 | 100 | 100 |
| | 50 | 100 | 100 |
| 4 hour | 200 | 0 | 100 |
| | 100 | 10 | 80 |
| | 50 | 0 | 50 |
| NO TREATMENT | | 20 | |

[a]Mice were treated subcutaneously at one or four hours before intraperitoneal injection of $2 \times 10^8$ CFU of S. aureus. There were 10 mice in each group.

We claim:

1. A high ratio cephalosporin:lipid complex comprising a lipid and a cephalosporin wherein the complex is at least 20% (w/w) cephalosporin.

2. The complex of claim 1 herein said lipid is a rigid lipid.

3. The complex of claim 1 wherein the complex is at least about 30% (w/w) cephalosporin.

4. The complex of claim 3 wherein the complex is at least about 40% (w/w) cephalosporin.

5. The complex of claim 4 wherein the complex is at least about 50% (w/w) cephalosporin.

6. The complex of claim 1 wherein the lipid comprises a head group and two carbon chains said chains are saturated and of a length of at least about 16 carbon units.

7. The complex of claim 6 wherein the lipid is dipalmitoylphosphatidylcholine.

8. The complex of claim 7 wherein said dipalmitoylphosphatidylcholine comprises up to about 80% (w/w) of the complex.

9. The complex of claim 1 wherein the cephalosporin is cefazolin, cephapirin, cephalothin, cefaclor, cephaloridine, cephoxazole, cefoxitin, cephradine, cephalexin, cephaloglycine, cefuroxime, cefmenoxime or cephalonium.

10. The complex of claim 9 wherein the cephalosporin is cefazolin.

11. A method of bacterial infection prophylaxis in an animal, including a human, comprising the step of administering to said animal a bacterial infection prophylaxis effective amount of a high ratio cephalosporin:lipid complex, wherein the complex is at least 30% (w/w) cephalosporin.

12. The method of claim 1 wherein the lipid is a rigid lipid.

13. The method of claim 11 further comprising about two administrations each day or less.

14. The method of claim 12 further comprising maintaining over an extended period an available cephalosporin level of at least a minimum inhibitory concentration ("MIC") of the cephalosporin in said animal.

15. The method of claim 14 wherein the the cephalosporin level is at least about 4 times the MIC.

16. The method of claim 14 wherein the MIC is measured as a blood plasma or serum level.

17. The method of claim 14 wherein the MIC is measured as a tissue level.

18. The method of claim 11 wherein the administration is intramuscularly, intraperitoneally, intravenously or subcutaneously.

19. The method of claim 11 wherein the cephalosporin comprises cefazolin, cephapirin, cephalothin, cefaclor, cephaloridine, cephoxazole, cefoxitin, cephradine, cephalexin, cephaloglycine, cefuroxime, cefmenoxime or cephalonium.

20. The method of claim 19 wherein the cephalosporin comprises cefazolin further comprising administering said cefazolin at a dosage of about 20–150 mg base weight per kilogram animal body weight per day.

21. The method of claim 19 wherein the cephalosporin comprises cefazolin and the maintained available cephalosporin level of cefazolin is at least about 0.5 ug (base weight)/ml plasma or at least about 0.5 ug (base weight)/mg tissue (RES).

22. The method of claim 21 wherein the maintained available cephalosporin level of cefazolin comprises at least about 5 ug (base weight)/ml plasma or 5 ug (base weight)/mg tissue (RES).

23. The method of claim 22 wherein the maintained cephalosporin level of cefazolin comprises at least about 50 ug/ml plasma or 50 ug (base weight)/mg tissue (RES).

24. A method of claim 11 wherein the infection prophylaxis is to bacteremia.

25. The method of claim 24 further comprising about two administrations each day or less.

26. The method of claim 24 further comprising maintaining over an extended period an available cephalosporin level of at least a minimum inhibitory concentration ("MIC") of the cephalosporin in said animal.

27. The method of claim 26 wherein the administration maintains an cephalosporin level of at least about 4 times the MIC.

28. The method of claim 26 wherein the MIC is measured as a blood plasma level.

29. The method of claim 26 wherein the MIC is measured as a tissue level.

30. The method of claim 26 wherein the administration is intramuscularly, intraperitoneally, intravenously or subcutaneously.

31. The method of claim 26 wherein the cephalosporin comprises cefazolin, cephapirin, cephalothin, cefaclor, cephaloridine, cephoxazole, cefoxitin, cephradine, cephalexin, cephaloglycine, cefuroxime, cefmenoxime or cephalonium.

32. The method of claim 31 wherein the cephalosporin comprises cefazolin further comprising administering said cefazolin at a dosage of about 20–150 mg (base weight) per kilogram animal body weight per day.

33. The method of claim 31 wherein the cephalosporin comprises cefazolin and the maintained available cephalosporin level of cefazolin is at least about 0.5 ug (base weight)/ml plasma or 0.5 ug (base weight)/mg tissue (RES).

34. The method of claim 33 wherein the cephalosporin comprises cefazolin and the maintained available cephalosporin level of cefazolin is at least about 5 ug/ml plasma or 5 ug (base weight)/mg tissue (RES).

35. The method of claim 34 wherein the maintained cephalosporin level of cefazolin is at least about 50 ug/ml plasma or 50 ug (base weight)/mg tissue (RES).

36. A method of claim 11 wherein the infection prophylaxis is against disseminated bacterial infections involving the reticulo-endothelial system.

37. The method of claim 36 further comprising about two administrations each day or less.

38. The method of claim 36 further comprising maintaining over an extended period an available cephalosporin level of at least a minimum inhibitory concentration ("MIC") of the cephalosporin in said animal.

39. The method of claim 38 wherein the cephalosporin level is at least about 4 times the MIC.

40. The method of claim 38 wherein the MIC is measured as a blood plasma level.

41. The method of claim 38 wherein the MIC is measured as a tissue level.

42. The method of claim 38 wherein the administration is intramuscularly, intraperitoneally, intravenously or subcutaneously.

43. The method of claim 38 wherein the cephalosporin comprises cefazolin, cephapirin, cephalothin, cefaclor, cephaloridine, cephoxazole, cefoxitin, cephradine, cephalexin, cephaloglycine, cefuroxime, cefmenoxime or cephalonium.

44. The method of claim 43 wherein the cephalosporin comprises cefazolin further comprising administering said cefazolin at a dosage of about 20–150 mg (base weight) per kilogram animal body weight per day.

45. The method of claim 43 wherein the cephalosporin comprises cefazolin and the maintained available cephalosporin level of cefazolin is at least about 0.5 ug (base weight)/ml plasma or 0.5 ug (base weight)/mg tissue (RES).

46. The method of claim 45 wherein the maintained available cephalosporin level of cefazolin is at least about 5 ug/ml plasma or 5 ug (base weight)/mg tissue (RES).

47. The method of claim 46 wherein the maintained cephalosporin level of cefazolin is at least about 10 ug/ml plasma or 10 ug (base weight)/mg tissue (RES).

48. The method of claim 36 wherein the bacterial infection prophylaxis is against the bacteria *Mycobacterium sp.* or *Salmonella sp.*

49. The method of claim 36 wherein the bacterial infection prophylaxis is against osteomyelitis.

* * * * *